US010398773B2

(12) United States Patent
Guelen et al.

(10) Patent No.: US 10,398,773 B2
(45) Date of Patent: Sep. 3, 2019

(54) PORCINE PARVOVIRUS

(71) Applicant: Intervet Inc., Madison, NJ (US)

(72) Inventors: Lars Guelen, Nijmegen (NL); Ad de Groof, Groesbeek (NL); Carla Christina Schrier, Boxmeer (NL); Martin Deijs, Huizen (NL); Cornelia Maria Hoek Van Der, Diemen (NL)

(73) Assignee: Intervet Inc., Madison, NJ (US)

(*) Notice: Subject to any disclaimer, the term of this patent is extended or adjusted under 35 U.S.C. 154(b) by 0 days.

(21) Appl. No.: 15/304,099

(22) PCT Filed: Apr. 16, 2015

(86) PCT No.: PCT/EP2015/058221
§ 371 (c)(1),
(2) Date: Oct. 14, 2016

(87) PCT Pub. No.: WO2015/158798
PCT Pub. Date: Oct. 22, 2015

(65) Prior Publication Data
US 2017/0056492 A1 Mar. 2, 2017

(30) Foreign Application Priority Data
Apr. 17, 2014 (EP) .................................... 14165255

(51) Int. Cl.
*A61K 39/23* (2006.01)
*C07K 16/08* (2006.01)
*C12N 7/00* (2006.01)
*A61K 39/00* (2006.01)

(52) U.S. Cl.
CPC ............ *A61K 39/23* (2013.01); *C07K 16/081* (2013.01); *C12N 7/00* (2013.01); *A61K 2039/5252* (2013.01); *A61K 2039/5254* (2013.01); *A61K 2039/552* (2013.01); *C12N 2750/14321* (2013.01); *C12N 2750/14322* (2013.01); *C12N 2750/14334* (2013.01)

(58) Field of Classification Search
None
See application file for complete search history.

(56) References Cited

U.S. PATENT DOCUMENTS

2014/0170180 A1* 6/2014 Iyer ...................... C07K 14/005
424/186.1
2017/0056492 A1* 3/2017 Guelen ................ C07K 16/081

FOREIGN PATENT DOCUMENTS

CN 102965345 A 3/2013
WO 2011047158 A1 4/2011
WO 2011107534 A1 9/2011
WO 2014099669 A1 6/2014

OTHER PUBLICATIONS

Sequence alignment of instant SEQ ID No. 1 of Published_Applicationd_NA_Main with SEQ ID No. 1 of U.S. Appl. No. 13/796,621 by Iyer et al filed Mar. 12, 2013.*
Sequence alignment of instant SEQ ID No. 3 of Published_Applicationd_NA_Main with SEQ ID No. 1 of U.S. Appl. No. 13/796,621 by Iyer et al filed Mar. 12, 2013.*
Sequence alignment of SEQ ID No. 1 w GenEmbl database access No. KF999685 by Ni et al in J of Virol vol. 11 No. 1 submitted Dec. 2013.*
Sequence alignment of SEQ ID No. 3 w GenEmbl database access No. KF999685 by Ni et al in J of Virol vol. 11 No. 1 submitted Dec. 2013.*
Martinez et al. (Vaccine. 1992; 10 (10) 684-690, abstract only).*
Labuscagne et al. (Journal of South African Veterinary Association. Dec. 2012; 83 (1), Art #19. http://dx.doi.org/10.4102/jsava.v83i1.19).*
Navotny et al. (Acta Veterinaria-Beograd 2016; 66 (1): 138-146).*
Grahofer et al. (Porcine Health Management. 2017; 3 (27): 6 pages.*
Cságola, A. et al., Detection, prevalence and analysis of emerging porcine parvovirus infections, Arch. Virol., 2012, pp. 1003-1010, vol. 157.
European Search Report for 14165255.2, dated Oct. 21, 2014, 8 pages.
International Search Report for PCT/EP2015/058221 dated Jul. 16, 2015, 12 pages.
XP002730565 retrieved from EBI accession No. EM-STD:KF999685.
XP002730566, retrieved from EBI accession No. EM_STD:KF999683.
Chen, C. et al., Generation and Analysis of Random Point Mutations in an Antibody CDR2 Sequence: Many Mutated Antobodies Lose their Ability to Bind Antigen, J. Exp. Med., 1992, pp. 855-866, vol. 176.
Ohno, S et al., Antigen-binding specificities of antibodies are primarily determined by seven residues of Vh, Proc. Natl. Acad., 1985, pp. 2945-2949, 82.
Rudikoff, S et al., Single amino acid substitution altering antigen-binding specificity, PNAS, 1982, pp. 1979-1983, 79.

* cited by examiner

*Primary Examiner* — Shanon A. Foley
(74) *Attorney, Agent, or Firm* — Sarah L. Hooson; Catherine D. Fitch

(57) ABSTRACT

The present invention relates to a novel porcine parvovirus, to proteins of the virus and to vaccines based upon the virus and proteins thereof. The invention also relates to DNA fragments comprising a gene of the virus and to DNA vaccines based upon genes of the virus. Further the invention relates to antibodies that are reactive with the novel virus and to diagnostic tests for the detection of the virus or antibodies against the virus.

11 Claims, 3 Drawing Sheets

Figure 1:
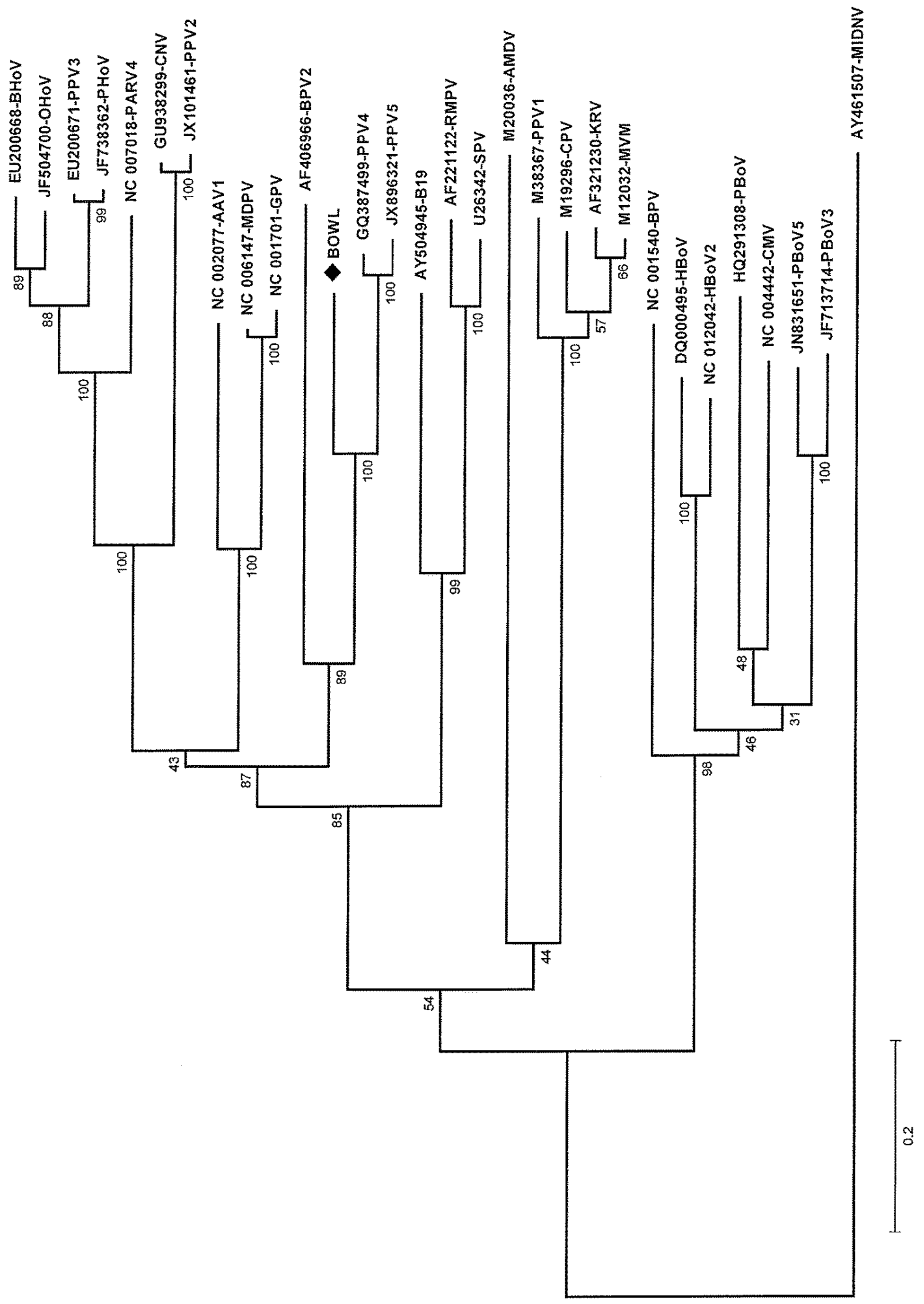

Specification includes a Sequence Listing.

PORCINE PARVOVIRUS

CROSS-REFERENCE TO RELATED APPLICATIONS

This application is a national stage entry under 35 U.S.C. § 371 of PCT/EP2015/058221 filed on Apr. 16, 2015, which claims priority to EP Application No. EP14165255.2 filed on Apr. 17, 2014. The content of PCT/EP2015/14165255.2 is hereby incorporated by reference in its entirety.

The present invention relates to a novel porcine parvovirus, to proteins of the virus and to vaccines based upon the virus and proteins thereof. The invention also relates to DNA fragments comprising a gene of the virus and to DNA vaccines based upon genes of the virus. Further the invention relates to antibodies that are reactive with the novel virus and to diagnostic tests for the detection of the virus or antibodies against the virus.

Over the last decades, world-wide a strong increase is seen in the consumption of pig meat. As a consequence, an increase is seen in the number and the size of farms, in order to meet the increasing needs of the market. As is known from animal husbandry in general, large numbers of animals living closely together are vulnerable to all kinds of diseases, even diseases hardly known or seen or even unknown before the days of large-scale commercial farming.

One of the diseases in pigs that has been known for over 60 years now is haemorrhagic bowel syndrome (HBS). This disease is referred to as a syndrome due to the fact that the cause of the disease is not clear and the consistency of the various clinical signs is not always fully clear.

HBS is a disease that occurs in infrequent, explosive outbreaks. Rapidly growing swine of 4-6 months old are primarily affected. In most cases, the disease is observed in fattening pigs. Pigs die suddenly without evidence of diarrhea, although the extent of mortality varies[1-3]. Swiss autopsy data, based on more than 16000 pigs, showed an incidence of HBS of 2.66%. In the USA, HBS is reported to cause 0.5%-7% of all mortalities during the growth-finish phase[3].

Hemorrhagic bowel syndrome should not be seen as a single disease with a single cause.

The most prominent symptom of HBS is intestinal hemorrhages, often accompanied by intestinal *volvulus* (torsions of the intestine). However, these symptoms are also an indication for gastric ulcers and ileitis, which complicates the diagnosis of HBS. Rotation of the entire intestine may occur, causing blood to pool and stagnate. Intestinal *volvulus* can be observed in up to 80% of the HBS cases[1-3]. Other frequently noticed symptoms of the disease are thin intestinal walls, and bloody fluid in the intestines.

The precise etiology of HBS is unclear. As indicated above, rather than having a single cause, the etiology of the syndrome is most likely multifactorial. Stress, several environmental and management aspects may play a role. Predisposing factors may include vigorous exercise, handling, fighting, piling, or irregular feeding. There is no conclusive evidence that an infectious agent (bacterial or viral) can cause HBS[1,3], although *Clostridium* sp. and *E. coli* have been isolated from animals suffering from HBS. Attempts to reproduce disease by administering filtered intestinal contents from animals suffering from HBS, intravenously or orally, to healthy animals failed. Attempts to reproduce disease by oral inoculation of *E. coli* and *Clostridium perfringens* type A isolated from infected swine equally failed.

On the other hand it is known that the frequency of the disease can be lowered to a certain extent by the administration of antibiotics in the feed. This strengthens the idea that the disease is indeed multifactorial: a combined effect of e.g. stress, and one or more pathogens.

It is an objective of the present invention to provide a new infectious agent associated with this disease as well as vaccines aiming at combating the disease or at least decreasing the mortality of the disease. Moreover, it is an objective of the present invention to provide means to detect and identify the disease-associated infectious agent.

Recently, HBS-diagnosed pigs were collected from several farms during an outbreak of disease in Mexico.

The affected pigs didn't have previous symptoms of disease and died suddenly, between 2 and 6 hours after first signs of illness.

On necropsy the pigs showed abnormalities in small intestine, i.a. hemorrhagic symptoms, a thin intestinal wall and bloody fluids in the intestines. No abnormalities were found in other organs, except for observations of enlarged, swollen reddish lymph nodes. The disease was confirmed as HBS.

Samples from necropsied affected pigs from various farms were analysed for the presence of viruses and surprisingly a novel virus was found in 76% of the animals. The fact that the virus was not detected in all animals may have to do with the amount of time passed between the death of the animals and the moment they were submitted to post-mortem section. This can i.a. be concluded from the fact that the amounts of virus found per animal varied to a great extent. It is contemplated by the inventors that in the pigs in which the virus is seemingly absent, this is likely due to the fact that the amount of virus present was in those pigs below the detection level at the moment of analysis. Furthermore, the site of initial virus replication is not known for this novel virus, and thus the primary site of virus replication after infection may not have been sampled.

Since the novel virus was detected in these HBS-diagnosed pigs, the virus will be further referred to as HBS-associated virus. Haemorrhagic bowel syndrome can now be characterized by the presence of the novel virus according to the invention at some stage during the disease in organs of animals suffering from HBS, in combination with the following clinical symptoms: intestinal hemorrhages, often accompanied by intestinal *volvulus*, thin intestinal walls and bloody fluids in the intestines.

The sequence of the viral genome was analysed and revealed that the novel virus bears some albeit a relatively low level of resemblance to a recently identified genus of the Parvovirinae subfamily within the Parvoviridae.

Parvoviruses are linear, non-segmented single-stranded DNA viruses, with an average genome size of 5000 nucleotides and a size in the range of 18-26 nm in diameter.

The almost full length DNA sequence of a representative of the new porcine parvovirus is presented in SEQ ID NO: 10.

The novel virus comprises two large Open Reading Frames (ORFs): ORF1 encoding nonstructural protein 1 (NS1) consisting of 662 amino acids is found at position 0134-2122 of SEQ ID NO: 10 and ORF2 encoding Capsid Protein (CP) consisting of 1189 amino acids is found at position 2130-5699 of SEQ ID NO: 10.

An example of the DNA sequence of ORF2, the gene encoding the Capsid Protein, is depicted in SEQ ID NO: 1. SEQ ID NO: 2 represents the amino acid sequence of the Capsid Protein.

An example of the DNA sequence of ORF1 encoding nonstructural protein NS1 is depicted in SEQ ID NO: 3. SEQ ID NO: 4 represents the amino acid sequence of the nonstructural protein NS1.

The sub-family of the Parvovirinae currently comprises 7 genera[15]:

1) PARV4-like virus
2) Erythrovirus
3) Bocavirus
4) Dependovirus
5) Amdovirus
6) Parvovirus
7) A newly proposed parvo clade At this moment, six different parvoviruses have been identified that infect pigs:

a) Classic porcine parvovirus type 1 (PPV1), a member of the genus Parvovirus
b) porcine parvovirus type 2 (PPV2), a member of the genus PARV4-like virus
c) porcine parvovirus type 3 (PPV3, also known as porcine PARV4, hokovirus or partetravirus), also a member of the genus PARV4-like virus
d) porcine parvovirus type 4 (PPV4), a member of the newly proposed Clade
e) porcine parvovirus type 5 (PPV5), also a member of the newly proposed Clade
f) porcine bocavirus (PBoV), a member of the genus Bocavirus PPV1 is known to be the causative agent of SMEDI, a syndrome connected with stillbirth, mummification, embryonic death and infertility.[4,5]

PPV2 is not known to cause disease as such, but is suggested to be a co-factor in the development of Porcine Circovirus Associated Disease (PCVAD)[6,7].

PPV3 is also not known to cause disease as such, but is possibly also a co-factor in the development of Porcine Circovirus Associated Disease (PCVAD)[8-11].

PPV4 was isolated originally from lung tissue of pigs. The tissue appeared to be co-infected with porcine circovirus. Is not known to cause disease and has also not convincingly been associated with a disease caused by another pathogen[12-14].

PPV5 is also not known to cause any symptoms or lesions and is not associated with a disease caused by another pathogen[15-16].

Porcine Bocavirus is a relatively new type of porcine parvovirus for which clinical significance and epidemiology are largely unexplored yet[17].

The amino acid sequences of ORF1 and ORF2 of the novel virus were used to make phylogenetic trees based on the Maximum Likelihood method, the Poisson correction model and bootstrap analysis (500 replicates).

These trees were made using the program MEGA, version 5, using standard settings. (MEGA5: Molecular Evolutionary Genetics Analysis Using Maximum Likelihood, Evolutionary Distance, and Maximum Parsimony Methods. Koichiro Tamura, Daniel Peterson, Nicholas Peterson, Glen Stecher, Masatoshi Nei and Sudhir Kumar. Mol. Biol. Evol. 28(10): 2731-2739. 2011 doi:10.1093/molbev/msr121 Advance Access publication May 4, 2011).

Figure 2:
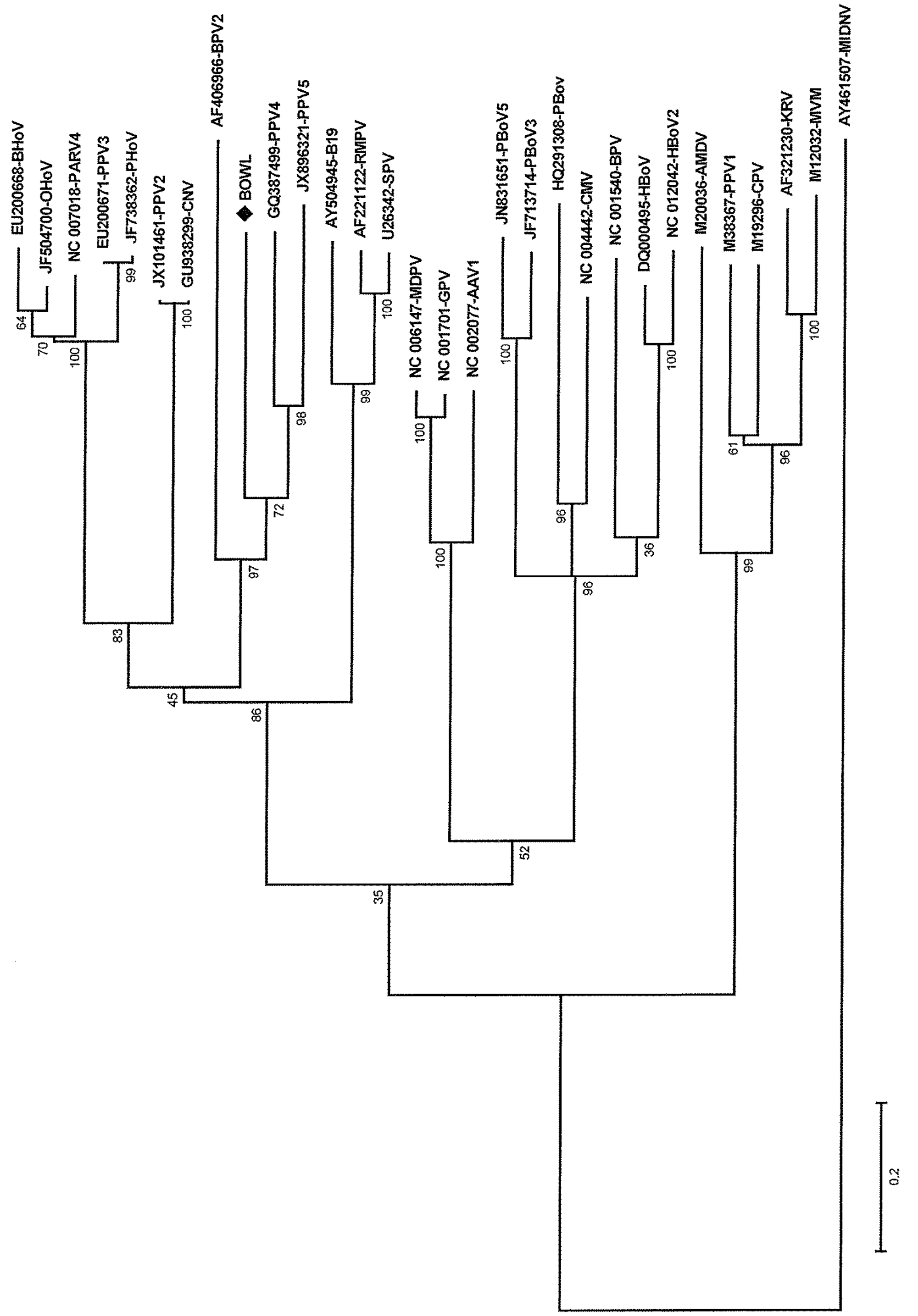

The phylogenetic tree of ORF1 is presented in FIG. 1, that of ORF2 in FIG. 2. The percentage bootstrap support is specified at the nodes. Distance bars indicate the number of nucleotide substitutions per site.

As follows from these phylogenetic trees, the novel porcine parvovirus is more related to Porcine Parvovirus 5 (PPV5) and Porcine Parvovirus 4 (PPV4) than to PPV1, 2 or 3, or the Bocaviruses. It was found that both the NS1 coding sequence and the Capsid Protein coding sequence shows a certain fit in that part of the Parvovirinae phylogenetic tree that also comprises the unrelated viruses PPV4 and PPV5.

For this reason the inventors decided to tentatively place the novel virus in the group of the new Clade viruses.

However, the sequence identity with existing Porcine parvoviruses even within the group of the new Clade virus is relatively low. For this reason it is even conceivable that the novel virus belongs to a new genus within the family Parvovirinae.

SEQ ID NO: 1 and 3 show typical examples of the nucleotide sequence of the genes encoding the Capsid Protein and the nonstructural protein NS1 of a virus according to the invention.

It will be understood that for these proteins natural variations can exist between individual representatives of the HBS-associated virus. Genetic variations leading to minor changes in e.g. the Capsid Protein sequence do exist. This is equally true for the NS1 gene. First of all, there is the so-called "wobble in the second and third base" explaining that nucleotide changes may occur that remain unnoticed in the amino acid sequence they encode: e.g. triplets TTA, TTG, TCA, TCT, TCG and TCC all encode Leucine. In addition, minor variations between representatives of the novel porcine parvovirus according to the invention may be seen in amino acid sequence. These variations can be reflected by (an) amino acid difference(s) in the overall sequence or by deletions, substitutions, insertions, inversions or additions of (an) amino acid(s) in said sequence Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science 227, 1435-1441, 1985) and determining the functional similarity between homologous proteins. Such amino acid substitutions of the exemplary embodiments of this invention, as well as variations having deletions and/or insertions are within the scope of the invention.

This explains why the Capsid Protein and the nonstructural protein NS1, when isolated from different representatives of a porcine parvovirus according to the invention, may have homology levels that are significantly below 100%, while still representing the Capsid Protein and the nonstructural protein NS1 of the porcine parvovirus according to the invention.

This is clearly reflected e.g. in the phylogenetic tree in FIG. 1 of a paper by Xiao et al.,[6] where it is shown that even within one single genus the PARV4-like virus genus consisting of highly related parvoviruses nevertheless have significantly different overall genomic nucleotide sequences as well as significantly different NS1 gene nucleotide sequences.

Thus, the virus according to the invention is described i.a. as an isolated virus which is a member of the sub-family Parvovirinae of the family of the Parvoviridae, said virus being characterized in that a) the virus is an HBS-associated virus and b) the virus has a viral genome comprising a gene encoding a Capsid Protein (CP), wherein the nucleotide sequence of the CP gene has a level of identity of at least 80% to the nucleotide sequence as depicted in SEQ ID NO: 1.

For the purpose of this invention, a level of identity is to be understood as the level of identity of the sequence of SEQ ID NO: 1 and the corresponding region encoding the Capsid Protein of a porcine parvovirus of which the level of identity has to be determined.

A suitable program for the determination of a level of identity is the nucleotide blast program (blastn) of NCBI's Basic Local Alignment Search Tool, using the "Align two or more sequences" option and standard settings (blast.ncbinlm.nih.gov/Blast.cgi).

For the purpose of this invention, isolated means: set free from tissue with which the virus is associated in nature. An example of an isolated virus is the virus as present in cell culture.

A preferred form of this embodiment relates to a virus that has a Capsid Protein gene that has a level of identity of at least 82%, more preferably 84%, 86%, 88%, 90%, 91%, 92%, 93%, 94%, 95%, 96%, 97%, 98%, 99% or even 100%, in that order of preference, to the nucleotide sequence of the Capsid Protein as depicted in SEQ ID NO: 1.

An alternative way to describe the virus according to the present invention relates to the sequence of the NS1 gene of the virus.

SEQ ID NO: 3 shows a typical example of the nucleotide sequence of the NS1 gene of a virus according to the invention. As explained above, natural variations leading to minor changes in the NS1 sequence are however found.

Thus, a virus according to the invention can thus also be described as an isolated virus which is a member of the sub-family Parvovirinae of the family of the Parvoviridae, said virus being characterized in that a) the virus is an HBS-associated virus and b) the virus has a viral genome comprising a gene encoding a non-structural protein 1 (NS1), wherein the nucleotide sequence of the NS1 gene has a level of identity of at least 80% to the nucleotide sequence as depicted in SEQ ID NO: 3.

A preferred form of this embodiment relates to such a virus that has an NS1 gene that has a level of identity of at least 82%, more preferably 84%, 86%, 88%, 90%, 91%, 92%, 93%, 94%, 95%, 96%, 97%, 98%, 99% or even 100%, in that order of preference, to the nucleotide sequence of the NS1 gene as depicted in SEQ ID NO: 3.

Thus, in summary a virus according to the present invention is an isolated virus which is a member of the sub-family Parvovirinae of the family of the Parvoviridae, said virus being characterized in that a) the virus is an HBS-associated virus and b) the virus has a viral genome comprising a gene encoding a Capsid Protein (CP) and a gene encoding a non-structural protein 1 (NS1), wherein the nucleotide sequence of the CP gene has a level of identity of at least 80% to the nucleotide sequence as depicted in SEQ ID NO: 1 or the nucleotide sequence of the NS1 gene has a level of identity of at least 80% to the nucleotide sequence as depicted in SEQ ID NO: 3.

A preferred form of this embodiment relates to an isolated virus which is a member of the sub-family Parvovirinae of the family of the Parvoviridae, said virus being characterized in that a) the virus is an HBS-associated virus and b) the virus has a viral genome comprising a gene encoding a Capsid Protein (CP) and a gene encoding a non-structural protein 1 (NS1), wherein the nucleotide sequence of the CP gene has a level of identity of at least 80% to the nucleotide sequence as depicted in SEQ ID NO: 1 and the nucleotide sequence of the NS1 gene has a level of identity of at least 80% to the nucleotide sequence as depicted in SEQ ID NO: 3.

Still another, alternative, way to characterize the virus according to the invention depends on a PCR-test using primer sets that are specific for the Capsid Protein gene sequence or the NS1 gene sequence of a virus according to the invention. Two different primer sets of which the sequence is depicted in SEQ ID NO: 5-6 and SEQ ID NO: 7-8 were elected for their specificity for the virus. The PCR-test using the first primer set (SEQ ID NO: 5-6) that specifically reacts with the Capsid Protein gene of the virus uses the two primers Bowl_Q_ORF2_FW: CTACATCTGCGCCTGAC (SEQ ID NO: 5) and Bowl_Q_ORF2_REV: GTGGTGAGAAGGCAAGAC (SEQ ID NO: 6), For Quantitative (Q)-PCR experiments, the PCR probe Bowl_Q_ORF2_PROBE: 6FAMCACGAGCTAGAGCGTGCTAAACAG-BHQ1 (SEQ ID NO: 9) is used in addition to these two primers.

The PCR-test using the second primer set (SEQ ID NO: 7-8) specifically reacts with the NS1 gene of the virus and uses the two primers Bowl_ORF1_7_7_4_F: TGTTGAGTGTGGTGGATTGG (SEQ ID NO: 7) and BowlORF11 6 2 6_R: AAGGAAGCTGGACCGAGAG (SEQ ID NO: 8).

The tests, which are described in more detail in the Examples section, are standard PCR tests.

If a member of the of the subfamily of the Parvovirinae subfamily within the Parvoviridae is analysed using the primer sets described above, the following can be said: if an analysis of the PCR-product of the first primer set reveals a PCR product of approximately 140 base pairs or if analysis of the PCR-product of the second primer set reveals a PCR product of approximately 853 base pairs, this unequivocally demonstrates that the analysed virus belongs to the virus according to the invention.

Merely as an example: a PCR product of approximately 853 base pairs is a PCR product with a length of between 853+10 and 853−10 base pairs. A PCR product of approximately 140 base pairs is a PCR product with a length of between 140+10 and 140−10 base pairs.

Thus again another form of this embodiment of the present invention relates to an isolated virus which is a member of the of the subfamily of the Parvovirinae subfamily within the Parvoviridae, characterized in that:

a) the virus is an HBS-associated virus and b) the viral genomic DNA reacts in a PCR reaction with a primer set as depicted in SEQ ID NO: 5 and 6 to give a PCR product of 140+/−10 base pairs or reacts in a PCR reaction with a primer set as depicted in SEQ ID NO: 7 and 8 to give a PCR product of 853+/−10 base pairs.

A preferred form of this embodiment relates to a virus according to the invention wherein the viral genomic DNA reacts in a PCR reaction with a primer set as depicted in SEQ ID NO: 5 and 6 to give a PCR product of 140+/−10 base pairs and reacts in a PCR reaction with a primer set as depicted in SEQ ID NO: 7 and 8 to give a PCR product of 853+/−10 base pairs.

A more preferred form of this embodiment relates to a virus according to the invention wherein the virus has a viral genome comprising a gene encoding a Capsid Protein (CP) and a gene encoding a non-structural protein 1 (NS1), wherein the nucleotide sequence of the CP gene has a level of identity of at least 80% to the nucleotide sequence as depicted in SEQ ID NO: 1 or the nucleotide sequence of the NS1 gene has a level of identity of at least 80% to the nucleotide sequence as depicted in SEQ ID NO: 3 and wherein the viral genomic DNA reacts in a PCR reaction with a primer set as depicted in SEQ ID NO: 5 and 6 to give a PCR product of 140+/−10 base pairs and reacts in a PCR reaction with a primer set as depicted in SEQ ID NO: 7 and 8 to give a PCR product of 853+/−10 base pairs.

The virus according to the invention can be in a live, a live attenuated or an inactivated form.

As indicated above, the DNA sequences of the genes encoding the CP and NS1 of the virus have now been characterized. The identification of these genes is highly useful, since they can now be used i.a. as a basis for DNA-vaccines, for use in the preparation of subunit vaccines on the basis of these proteins or for diagnostic purposes, as will extensively be explained below.

Another embodiment of the present invention relates to a DNA fragment comprising a gene encoding a Capsid Protein characterized in that that gene has a level of identity of at least 80% to the nucleotide sequence of the CP gene as depicted in SEQ ID NO: 1.

A preferred form of this embodiment relates to such a DNA fragment comprising a gene having a level of identity of at least 82%, more preferably 84%, 86%, 88%, 90%, 91%, 92%, 93%, 94%, 95%, 96%, 97%, 98%, 99% or even 100%, in that order of preference, to the nucleotide sequence of the CP as depicted in SEQ ID NO: 1.

Again another embodiment of the present invention relates to a DNA fragment comprising a gene encoding an NS1 characterized in that that gene has a level of identity of at least 80% to the nucleotide sequence of the NS1 gene as depicted in SEQ ID NO: 3.

A preferred form of this embodiment relates to such a DNA fragment comprising a gene having a level of identity of at least 82%, more preferably 84%, 86%, 88%, 90%, 91%, 92%, 93%, 94%, 95%, 96%, 97%, 98%, 99% or even 100%, in that order of preference, to the nucleotide sequence of the NS1 as depicted in SEQ ID NO: 3.

Still another embodiment of the present invention relates to a CP characterized in that this CP is encoded by a DNA fragment encoding a CP according to the invention.

Such CPs of the virus according to the invention are highly suitable because they are suitable for use in vaccines, more specifically in subunit vaccines, they can be used to raise antibodies and they make diagnostic tests possible, as explained below.

A preferred form of this embodiment relates to a CP having the amino acid sequence as depicted in SEQ ID NO: 2.

Again another embodiment of the present invention relates to an NS1, characterized in that that NS1 is encoded by a DNA fragment encoding an NS1 according to the invention.

Such NS1's of the virus according to the invention are highly suitable i.a. because they make diagnostic tests possible, as explained below.

A preferred form of this embodiment relates to an NS1 having the amino acid sequence as depicted in SEQ ID NO: 4.

It is one of the merits of the present invention that it is now for the first time possible to follow the course of viral infection and to analyse the presence or absence of the novel virus in the various organs and body fluids of pigs suffering from HBS. This helped to gain more insight in the development of disease.

It is known that in the weeks or even days before an individual pig shows full clinical signs of HBS, no abnormalities are found. The average timing between the first symptoms and death of the animals is about 2-6 hours. Shortly before death, the animals seem to suffer from abdominal distension and some of them scream before dying. The animals on the farms that developed clinical signs were euthanized before they died of the disease.

On the various Mexican farms from which HBS-pigs were collected, the HBS-incidence varied between 1-2%.

A total of 33 euthanized HBS-diagnosed animals collected from different farms, one group of 17 aged between 18-27 weeks (Example 1) and one group of 16 aged between 12-26 weeks (Example 2), were analysed. PCR reactions with the primer sets as described above revealed that in group 1, 5 out of 14 sera (3 sera were missing from the collection) were found positive for the virus and one rectal swap was found positive. A total of 8 full blood samples was found positive, and 12 out of 15 lymph nodes were found positive. In group 2, 5 out of 16 sera were positive for the virus and one rectal swap was found positive. From a representative animal of each group (animal 2 group 1, animal 10 group 2), organs were analysed for the presence of the virus. It was found that all sampled organs including lymph nodes, lung, spleen, intestine, kidney and liver, as well as feces tested positive for the virus.

It is another merit of the present invention that it is now possible to infect healthy pigs with the novel virus and to examine the route of viral infection. With this aim, organ material and feces from HBS-animals were homogenized in tissue culture medium. The homogenates were freeze-thawed once (−70° C.), centrifuged and filtered on 5 μm, 0.45 μm and 0.22 μm filters to remove remaining tissue material.

An inoculum A was made of the following material of a representative animal: feces, lymph nodes, lung, spleen and intestine of animal 10 group 2.

An inoculum B was made of the following material of another representative animal: feces, lymph nodes, lung, kidney and liver of animal 2 group 1. Full details of these experiments are given in the Examples section below (Example 3).

The inoculums (A or B) were given as a 4×2 mL IM dose and an oral dose of 20 ml to a total of 4 Boars and 8 gilts (Landrace/high health status/SPF) of 12-14 weeks of age at time of inoculation as follows:

Group 1: five animals, of which three animals received inoculum A, two served as contact sentinels.

Group 2: four animals, of which three animals received inoculum B, one served as contact sentinel.

Group 3: three animals, all of which received inoculum B.

One animal (male) was sacrificed prior to inoculation and served as negative control. The animals were screened for presence of the novel virus in serum, feces, nasal swaps and eye swaps prior to inoculation.

Blood samples, rectal/nasal/eye swaps were taken at several time points. Full details of the animal experiments are given in the Examples section below.

It was found that in 6 out of 6 inoculated animals the virus could be detected in serum as well as in rectal, nasal and eye swaps at 7 days after inoculation. In all of the 3 non-inoculated animals, the sentinels, the virus could be detected in the serum at 14 days after the inoculation of the other animals. Rectal/nasal and eye swaps of all sentinel animals were positive at day 7 after inoculation (Example 3, groups 1,2). In 3 out of 3 sera of inoculated animals on day 3 post inoculation, virus was detected (Example 3, group 3).

Thus, although it is true that the incidence of HBS is reported to be relatively low, given the highly contagious nature of the virus in combination with its high speed of infection, it may be expected that by far most, if not all, pigs in farms where HBS occurs will experience an infection with the virus.

It is therefore highly advisable to vaccinate all animals in farms where HBS occurs, against infection with the HBS-associated porcine parvovirus according to the invention. Such vaccination would eradicate at least a viral component of the multifactorial syndrome. And this in turn would prevent or at least decrease the severity of the disease.

It is also one of the merits of the present invention that since the novel porcine parvovirus has now been isolated and associated with HBS, the virus and/or protective subunits of the virus can be used as the starting material for vaccination purposes.

Thus, another embodiment of the present invention relates to vaccines for combating HBS in pigs, wherein such vaccines comprise a virus according to the invention and a pharmaceutically acceptable carrier.

Examples of pharmaceutically acceptable carriers that are suitable for use in a vaccine according to the invention are sterile water, saline, aqueous buffers such as PBS and the like. In addition a vaccine according to the invention may comprise other additives such as adjuvants, stabilizers, anti-oxidants and others, as described below.

Combating in this respect should be interpreted in a broad sense: combating HBS is considered to comprise vaccination in order to prevent the signs of the disease as well as vaccination to diminish the signs of the disease as outlined above.

Therapeutic vaccination once the virus is diagnosed in an infected animal that is not yet suffering from the syndrome is of course equally efficient. Therapeutic vaccination after the syndrome is diagnosed would seem not efficient, given the very short time between first clinical signs and death.

A vaccine according to the invention may comprise the virus according to the invention in attenuated live or inactivated form.

Attenuated live virus vaccines, i.e. vaccines comprising the virus according to the invention in a live attenuated form, have the advantage over inactivated vaccines that they best mimic the natural way of infection. In addition, their replicating abilities allow vaccination with low amounts of viruses; their number will automatically increase until it reaches the trigger level of the immune system. From that moment on, the immune system will be triggered and will finally eliminate the viruses.

A live attenuated virus is a virus that has a decreased level of virulence when compared to virus isolated from the field. A virus having a decreased level of virulence is considered a virus that even in combination with other factors involved in HBS does not induce mortality in pigs.

Therefore, one preferred form of this embodiment of the invention relates to a vaccine comprising a virus according to the invention wherein said virus is in a live attenuated form.

Attenuated viruses can e.g. be obtained by growing the viruses according to the invention in the presence of a mutagenic agent, followed by selection of virus that shows a decrease in progeny level and/or in replication speed. Many such agents are known in the art.

Another very often used method is serial in vitro passage. Viruses then get adapted to the cell line used for the serial passage, so that they behave attenuated when transferred to the natural host again as a vaccine. Still another way of obtaining attenuated viruses is to subject them to growth under temperatures deviating from the temperature of their natural habitat. Selection methods for temperature sensitive mutants (Ts-mutants) are well-known in the art. Such methods comprise growing viruses in the presence of a mutagen followed by growth at a sub-optimal temperature and at the optimal temperature, titration of progeny virus on cell layers and visual selection of those plaques that grow slower at the optimal temperature. Such small plaques comprise slow-growing and thus desired live attenuated viruses.

Live attenuated vaccines for combatting porcine parvovirus type PPV have been described i.a. by Paul & Mengeling[32], by Paul & Mengeling[33] and by Fujisaki e& Murakami[34].

A possible disadvantage of the use of live attenuated viruses however might be that inherently there is a certain level of virulence left. This is not a real disadvantage as long as the level of virulence is acceptable, i.e. as long as the vaccine at least prevents the pigs from dying. Of course, the lower the rest virulence of the live attenuated vaccine is, the less influence the vaccination has on weight gain during/after vaccination.

Inactivated vaccines are, in contrast to their live attenuated counterparts, inherently safe, because there is no rest virulence left. In spite of the fact that they usually comprise a somewhat higher dose of viruses compared to live attenuated vaccines, they may e.g. be the preferred form of vaccine in pigs that are suffering already from other diseases. Pigs that are kept under sub-optimal conditions, such as incomplete nutrition or sub-optimal housing would also benefit from inactivated vaccines.

Therefore, another preferred form of this embodiment relates to a vaccine comprising a virus according to the invention wherein said virus is in an inactivated form.

It is known that whole inactivated parvoviruses in general, be it porcine or canine parvoviruses, are an very efficient and safe basis for vaccines. Merely as an example: MSD AH (Boxmeer, The Netherlands) produces a commercially available inactivated porcine parvovirus type PPV vaccine: Porcilis Parvo. Hipra (Spain) also produces a commercially available inactivated porcine parvovirus type PPV vaccine: PARVOSUIN® MR/AD. Zoetis produces an inactivated Canine parvovirus: PARVAC and an inactivated porcine parvovirus type PPV vaccine: Porcine PARVAC. Novartis provides methods for the inactivation of parvovirus in U.S. Pat. No. 4,193,991.

Such inactivated whole virus vaccines can equally be made for the novel porcine parvovirus according to the invention. As is the case for known parvovirus vaccines, the production basically comprises the steps of growing the novel parvovirus on susceptible porcine cells, harvesting the virus, inactivating the virus and mixing the inactivated virus with a pharmaceutically acceptable carrier.

The standard way of inactivation is a classical treatment with formaldehyde. Other methods well-known in the art for inactivation are UV-radiation, gamma-radiation, treatment with binary ethylene-imine, thimerosal and the like. The skilled person knows how to apply these methods. Preferably the virus is inactivated with β-propiolactone, glutaraldehyde, ethylene-imine or formaldehyde. It goes without saying that other ways of inactivating the virus are also embodied in the present invention.

As indicated above, the virus can be grown in cell culture on susceptible porcine cells or cell lines.

Thus, another embodiment of the invention relates to a cell culture comprising a HBS-associated porcine parvovirus according to the present invention. Examples of cells and cell lines are SK6, PK15, primary or immortalized porcine kidney cells, primary or immortalized porcine alveolar lung macrophages. Practically the whole viral genome of the novel porcine parvovirus has now been determined and the DNA sequence of a representative of the novel virus is presented in SEQ ID NO: 10. The Inverted Terminal Repeats (ITRs) of the genome are not presented here. Since parvoviruses by definition belong to the smallest viruses known, the whole ss-DNA encoding the parvovirus according to the invention can easily be made synthetically. For this reason, the parvovirus can easily be made in vivo using the viral DNA as starting material. The Inverted Terminal Repeats (ITRs) of the genome of other, known, parvovirus such as i.a. described by Qiu et al.[37] and by Wang et al.[38] can be used to complete the viral genome as presented in SEQ ID NO: 10. The ITRs merely play a role in the replication of the viral genome, and as such they are not relevant from an immunological point of view. Thus for the purpose of producing a virus according to the invention the ITRs are interchangeable.

Cloning of full-length parvoviral DNA into a plasmid such as e.g. Bluescript II SK, and the subsequent generation of whole parvovirus through transfection of porcine cells with an expression plasmid encoding the novel porcine parvovirus is i.a. described by Qiu et al.[37] and by Wang et al.[38]. A permissive cell line such as SK6, PK15, primary or immortalized porcine kidney cells, primary or immortalized porcine alveolar lung macrophages would be the preferred cell line for this purpose. Nevertheless, if desired non-permissive cell lines can also be used: the genome of the novel parvovirus can i.a. be replicated in non-permissive cells with the help of adenovirus genes as described by Guan et al.[39].

Although whole inactivated parvoviruses provide a good basis for vaccines, their production may be expensive, depending i. a. upon the type of host cells used, the substrate and the cell culture medium used. In the specific case of parvoviruses, an attractive alternative for the use of whole viruses is the use of parvovirus CP subunits, more preferably subunits in the form of so-called empty capsids.

Such empty capsids are basically virus-like particles that however do not comprise the parvoviral genome. As a consequence, parvoviral empty capsid particles do not have to be inactivated before use in a vaccine, and therefore they have the additional advantage that they are intrinsically safe.

Empty capsids can be obtained by mere expression of ORF2 encoding the Capsid Protein, in a suitable expression system. The so-formed capsid protein self-assembles into empty virus particles.

Parvoviral empty capsids can readily be made in large amounts and they are highly immunogenic.

By far most expression systems currently in use for making parvoviral empty capsids are baculovirus-based expression systems.

Methods for the production of highly immunogenic parvovirus empty capsids in baculovirus-based expression systems have been e.g. described for porcine parvovirus type PPV by Martinez[18], Casal[19], Zhou et al.[29] and by Hao Feng[21]. For other parvoviruses, such methods have been described e.g. by Saliki[22] and by Brown[23].

Furthermore, baculovirus expression systems and baculovirus expression vectors in general have been described extensively in textbooks such as by O'Reilly at al.[24] and Murhammer[25].

Baculovirus-based expression systems are also commercially available, e.g. from Invitrogen Corporation, 1600 Faraday Avenue, Carlsbad, Calif. 92008, USA.

An alternative for Baculovirus-based expression systems are yeast-based expression systems. Yeast expression systems are e.g. described by Gellissen et al.[29].

Ready-to-use expression systems are i.a. commercially available from Research Corp. Technologies, 5210 East Williams Circle, Suite 240, Tucson, Ariz. 85711-4410 USA. Yeast and insect cell expression systems are also e.g. commercially available from Clontech Laboratories, Inc. 4030 Fabian Way, Palo Alto, Calif. 94303-4607, USA.

Expression of the Capsid Protein is of course also possible in mammalian cell based expression systems as known in the art, but these systems would most likely be more expensive to use, when compared to the baculovirus-based expression systems.

Thus another form of this embodiment relates to a vaccine for combating HBS-associated porcine parvovirus in pigs, characterized in that said vaccine comprises an immunogenically effective amount of a Capsid Protein according to the invention and a pharmaceutically acceptable carrier.

A preferred form of this embodiment relates to a vaccine for combating HBS-associated porcine parvovirus in pigs, characterized in that said vaccine comprises an immunogenically effective amount of a Capsid Protein according to the invention in the form of empty capsids.

The amount of empty capsids in a vaccine and the route of administration would be comparable with that of inactivated whole virus particles, since in terms of immunogenicity and similarity of the capsid they are comparable to inactivated whole virus particles.

Usually, an amount of between 1 and 100 μg of the novel parvovirus empty capsids would be very suitable as a vaccine dose. From a point of view of costs, a preferred amount would be in the range of 1-50 μg of empty capsids, more preferred in the range of 1-25 μg.

Casal[19] describes that for both canine parvovirus and porcine parvovirus doses as low as 1-3 μg in the presence of conventional adjuvants confer total protection on the corresponding host against the disease.

A vaccine according to the invention on the basis of inactivated whole virus or empty capsids preferably comprises an adjuvant. Conventional adjuvants, well-known in the art are e.g. Freund's Complete and Incomplete adjuvant, vitamin E, non-ionic block polymers, muramyl dipeptides, Quill A®, mineral oil e.g. Bayol® of or Markol®, vegetable oil, and Carbopol® (a homopolymer), or Diluvac® Forte. The vaccine may also comprise a so-called "vehicle". A vehicle is a compound to which the polypeptide adheres, without being covalently bound to it. Often used vehicle compounds are e.g. aluminum hydroxide, -phosphate or -oxide, silica, Kaolin, and Bentonite.

Casal[19] successfully used i.a. aluminum hydroxide and Quill A in his parvovirus vaccines.

In principle a vaccine according to the invention can be given just once. However, especially in the case of inactivated vaccines, be it whole virus vaccines or empty capsid vaccines, preferably also a first and possibly a second booster vaccination is given. A first booster would usually be given at least two weeks after the first vaccination. A very suitable moment for a booster vaccination is between 3 and 16 weeks after the first vaccination. A second booster, if necessary, would usually be given between 4 and 50 weeks after the first booster.

An alternative to the inactivated whole virus vaccine approach and the empty capsid vaccine approach is the use of live recombinant non-parvovirus vectors that have pigs as their host animal, as carriers of the novel porcine parvoviral Capsid Protein gene.

Amongst the suitable recombinant non-parvovirus vectors that have pigs as their host animal, two vectors are especially suitable as carriers: Pseudorabies virus (PRV) and Classical Swine Fever Virus (CSFV). The use of such recombinant viruses in vaccines has the additional advantage that the vaccinated animals become at the same time vaccinated against both PRV and PPV or CSFV and PPV.

Chen et al.[27] describe the construction and use of a live attenuated PRV recombinant vector expressing a porcine parvovirus type PPV Capsid Protein. This PRV recombinant was administered to eight-day-old piglets in an amount of $5 \times 10^5$ $TCID_{50}$ and this amount of vaccine proved to be safe and provided an excellent immunity against both PRV and PPV.

Live attenuated CSFV vectors are also very suitable as live recombinant vectors. Merely as an example; live attenuated CSFV from which the $N^{pro}$ gene has been deleted, has been described by Mayer et al.[28] Such a live attenuated virus allows, i.a. at the site of the deletion of the $N^{pro}$ gene, for the insertion of the gene encoding the Capsid Protein. Such a live recombinant CSFV vector equally forms a suitable carrier for the novel porcine parvoviral Capsid Protein gene.

The expression of the Capsid Protein gene can be brought under the control of any suitable heterologous promoter that is functional in a mammalian cell (see below). A heterologous promoter is a promoter that is not the promoter responsible for the transcription of the CP gene in the wild-type form of the novel porcine parvovirus according to the invention. It may be a parvoviral promoter responsible for the transcription of a CP or NS1 of another parvovirus, that does not belong to the parvoviruses according to the invention or it may be a non-parvoviral promoter.

Therefore, another embodiment of the present invention relates to a DNA fragment comprising a gene encoding a CP according to the invention, characterized in that said gene is under the control of a functional heterologous promoter.

Chen et al[27] made use of the CMV promoter for driving the expression of the Capsid protein gene, but other suitable promoters that are functional in a mammalian cell are known in the art. A promoter that is functional in a mammalian cell is a promoter that is capable of driving the transcription of a gene that is located downstream of the promoter in a mammalian cell.

Examples of suitable promoters that are functional in a mammalian cell include classic promoters such as the (human) cytomegalovirus immediate early promoter (Seed, B. et al., Nature 329, 840-842, 1987; Fynan, E. F. et al., PNAS 90, 11478-11482, 1993; Ulmer, J. B. et al., Science 259, 1745-1748, 1993), Rous sarcoma virus LTR (RSV, Gorman, C. M. et al., PNAS 79, 6777-6781, 1982; Fynan et al., supra; Ulmer et al., supra), the MPSV LTR (Stacey et al., J. Virology 50, 725-732, 1984), SV40 immediate early promoter (Sprague J. et al., J. Virology 45, 773, 1983), the SV-40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2 and the β-actin promoter (Tang et al., Nature 356, 152-154, 1992). The regulatory sequences may also include terminator and poly-adenylation sequences. Amongst the sequences that can be used are the well-known bovine growth hormone poly-adenylation sequence, the SV40 poly-adenylation sequence, the human cytomegalovirus (hCMV) terminator and poly-adenylation sequences.

Thus another form of this embodiment relates to a vaccine for combating HBS-associated porcine parvovirus in pigs, characterized in that said vaccine comprises a live recombinant non-parvovirus vector comprising a DNA fragment comprising a gene encoding a CP according to the invention under the control of a functional promoter and a pharmaceutically acceptable carrier.

It goes without saying that the live recombinant non-parvovirus vector should be expressing an immunogenically effective amount of the Capsid Protein.

An alternative for vaccination with an inactivated whole virus vaccine, an empty capsid vaccine or a live recombinant non-parvovirus vector, is the use of DNA vaccination.

Such DNA vaccination is based upon the introduction of a DNA fragment carrying the gene encoding the Capsid Protein under the control of a suitable promoter, into the host animal. Once the DNA is taken up by the host's cells, the gene encoding the Capsid Protein is transcribed and the transcript is translated into Capsid Protein in the host's cells. This closely mimics the natural infection process of the parvovirus. Suitable promoters are promoters that are functional in mammalian cells, as exemplified above.

A DNA fragment carrying the gene encoding the Capsid Protein under the control of a suitable promoter could e.g. be a plasmid. This plasmid may be in a circular or linear form.

Examples of successful DNA vaccination of pigs are i.a. the successful vaccination against Aujeszky's disease as described in Gerdts et al.[30], Journal of General Virology 78: 2139-2146 (1997). They describe a DNA vaccine wherein a DNA fragment is used that carries glycoprotein C under the control of the major immediate early promoter of human cytomegalovirus. Vaccination was done four times with two weeks intervals with an amount of 50 μg of DNA. Vaccinated animals developed serum antibodies that recognized the respective antigen in an immunoblot and that exhibited neutralizing activity.

Another example of successful DNA vaccination of pigs is given by Gorres et al.[31]. They described successful DNA vaccination of pigs against both pandemic and classical swine H1N1 influenza. They vaccinated with a prime vaccination and 2 homologous boosts at 3 and 6 weeks post priming, of a DNA vaccine comprising the HA gene of influenza H1N1 under the control of a functional promoter.

Therefore, again another form of this embodiment relates to a vaccine for combating HBS-associated porcine parvovirus in pigs, characterized in that said vaccine comprises a DNA fragment comprising a gene encoding a Capsid Protein according to the present invention under the control of a functional promoter, and a pharmaceutically acceptable carrier.

It goes without saying that the DNA fragment comprising a gene encoding a Capsid Protein should be expressing an immunogenically effective amount of the Capsid Protein.

What constitutes an "immunogenically effective amount" for a vaccine according to the invention that is based upon a whole parvovirus according to the invention, an empty capsid according to the invention, a live recombinant vector or a DNA vaccine according to the invention depends on the desired effect and on the target organism.

The term "immunogenically effective amount" as used herein relates to the amount of parvovirus, empty capsid, live recombinant vector or DNA vaccine that is necessary to induce an immune response in pigs to the extent that it decreases the pathological effects caused by infection with a wild-type HBS-associated porcine parvovirus, when compared to the pathological effects caused by infection with a wild-type HBS-associated porcine parvovirus in non-immunized pigs.

It is well within the capacity of the skilled person to determine whether a treatment is "immunologically effective", for instance by administering an experimental challenge infection to vaccinated animals and next determining a target animal's clinical signs of disease, serological parameters or by measuring re-isolation of the pathogen, followed by comparison of these findings with those observed in field-infected pigs.

The amount of virus administered will depend on the route of administration, the presence of an adjuvant and the moment of administration.

A preferred amount of a live vaccine comprising virus according to the invention is expressed for instance as Tissue Culture Infectious Dose (TCID50). For instance for a live virus a dose range between 10 and $10^9$ TCID50 per animal dose may advantageously be used, depending on the rest virulence of the virus.

Preferably a range between $10^2$ and $10^6$ TCID50 is used.

Many ways of administration can be applied, all known in the art. Vaccines according to the invention are preferably administered to the animal via injection (intramuscular or via the intraperitoneal route) or per os.

The protocol for the administration can be optimized in accordance with standard vaccination practice. In all cases, administration through an intradermal injector (IDAL) is a preferred way of administration.

If a vaccine comprises inactivated virus or empty capsids according to the invention, the dose would also be expressed as the number of virus particles to be administered. The dose would usually be somewhat higher when compared to the administration of live virus particles, because live virus particles replicate to a certain extent in the target animal, before they are removed by the immune system. For vaccines on the basis of inactivated virus, an amount of virus particles in the range of about $10^4$ to $10^9$ particles would usually be suitable, depending on the adjuvant used.

If a vaccine comprises subunits, e.g. the CP according to the invention, the dose could also be expressed in micrograms of protein. For vaccines on the basis of subunits, a suitable dose would usually be in the range between 5 and 500 micrograms of protein, again depending on the adjuvant used.

If a vaccine comprises a DNA fragment comprising a gene encoding the Capsid Protein, the dose would be expressed in micrograms of DNA. For vaccines on the basis of subunits, a suitable dose would usually be in the range between 5 and 500 micrograms of DNA, i.a. depending on the efficiency of the expression plasmid used. In many cases an amount of between 20 and 50 micrograms of plasmid per animal would be sufficient for an effective vaccination.

A vaccine according to the invention may take any form that is suitable for administration in the context of pig farming, and that matches the desired route of application and desired effect. Preparation of a vaccine according to the invention is carried out by means conventional for the skilled person.

Oral routes are preferred when it comes to ease of administration of the vaccine.

For oral administration the vaccine is preferably mixed with a suitable carrier for oral administration i.e. cellulose, food or a metabolisable substance such as alpha-cellulose or different oils of vegetable or animal origin.

In practice, swine are vaccinated against a number of pathogenic viruses or micro-organisms.

Therefore it is highly attractive, both for practical and economic reasons, to combine a vaccine according to the invention for pigs with e.g. an additional immunogen of a virus or micro-organism pathogenic to pigs, or genetic information encoding an immunogen of said virus or micro-organism.

Thus, a preferred form of this embodiment relates to a vaccine according to the invention, wherein that vaccine comprises at least one other pig-pathogenic microorganism or pig-pathogenic virus and/or at least one other immunogenic component and/or genetic material encoding said other immunogenic component, of said pig-pathogenic microorganism or pig-pathogenic virus. An immunogen or immunogenic component is a compound that induces an immune response in an animal. It can e.g. be a whole virus or bacterium, or a protein or a sugar moiety of that virus or bacterium.

The most common pathogenic viruses and micro-organisms that are pathogenic for swine are *Brachyspira hyodysenteriae*, African Swine Fever virus, Nipah virus, Porcine Circovirus, Porcine Torque Teno virus, Pseudorabies virus, Porcine influenza virus, Porcine parvovirus, Porcine respiratory and Reproductive syndrome virus (PRRS), Porcine Epidemic Diarrhea virus (PEDV), Foot and Mouth disease virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae.*

Therefore, a more preferred form of the invention relates to a vaccine according to the invention, wherein the virus or micro-organism pathogenic to swine is selected from the group of *Brachyspira hyodysenteriae*, African Swine Fever virus, Nipah virus, Porcine Circovirus, Porcine Torque Teno virus, Pseudorabies virus, Porcine influenza virus, Porcine parvovirus, Porcine respiratory and Reproductive syndrome virus (PRRS), Porcine Epidemic Diarrhea virus (PEDV), Foot and Mouth disease virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae.*

Still another embodiment relates to a method for the preparation of a vaccine according to the invention, wherein the method comprises the mixing of a virus according to the invention and/or an empty capsid and/or a CP according to the invention and/or a DNA fragment encoding a CP according to the invention and/or a live recombinant non-parvovirus vector encoding a CP according to the invention, and a pharmaceutically acceptable carrier.

Again another embodiment of the present invention relates to a virus according to the invention and/or an empty capsid and/or a CP according to the invention and/or a DNA fragment encoding a CP according to the invention and/or a live recombinant non-parvovirus vector encoding a CP according to the invention, for use in a vaccine.

As mentioned above, the haemorrhagic bowel syndrome is a multifactorial syndrome. It is a compilation of factors that eventually trigger HBS. This means that it is important to know if the HBS-associated porcine parvovirus is present in a certain pig-population well before the first clinical signs become manifest. Thus, for efficient protection against disease, a quick and correct detection of the presence of the HBS-associated porcine parvovirus is important.

Therefore it is another objective of this invention to provide diagnostic tools suitable for the detection of HBS-associated porcine parvovirus.

These tools partially rely on the availability of antibodies against the virus. Such antibodies can e.g. be used in diagnostic tests for HBS-associated porcine parvovirus.

Antibodies or antiserum comprising antibodies against the HBS-associated porcine parvovirus according to the invention can quickly and easily be obtained through vaccination of e.g. pigs, poultry or e.g. rabbits with the virus according to the invention followed, after about four weeks, by bleeding, centrifugation of the coagulated blood and decanting of the sera. Such methods are well-known in the art.

Other methods for the preparation of antibodies raised against the HBS-associated porcine parvovirus, which may be polyclonal, monospecific or monoclonal (or derivatives thereof) are also well-known in the art. If polyclonal antibodies are desired, techniques for producing and processing polyclonal sera are well-known in the art for decades, see e.g. Mayer and Walter[35].

Monoclonal antibodies, reactive against the virus according to the invention can be prepared by immunizing inbred mice by techniques also long known in the art, see e.g. Kohler and Milstein[36].

Thus, another embodiment of the present invention relates to antibodies or antisera that are reactive with the virus according to the invention.

A diagnostic test kit based upon the detection of a virus according to the invention or antigenic material of that virus and therefore suitable for the detection of HBS-associated porcine parvovirus infection may e.g. comprise a standard ELISA test. In one example of such a test the walls of the wells of an ELISA plate are coated with antibodies directed against the virus. After incubation with the material to be tested, labeled antibodies reactive with the virus are added to the wells. If the material to be tested would indeed comprise the novel porcine parvovirus according to the invention, this virus would bind to the antibodies coated to the wells of the ELISA. Labeled antibodies reactive with the virus that would subsequently be added to the wells would in turn bind to the virus and a color reaction would then reveal the presence of antigenic material of the virus.

Therefore, still another embodiment of the present invention relates to diagnostic test kits for the detection of a virus according to the invention or antigenic material of the virus, that comprise antibodies reactive with a virus according to the invention or with antigenic material thereof. Antigenic material of the virus is to be interpreted in a broad sense. It can be e.g. the virus in a disintegrated form, or viral envelope material comprising viral outer membrane proteins. As long as the material of the virus reacts with antiserum raised against the virus, the material is considered to be antigenic material.

A diagnostic test kit based upon the detection in serum of antibodies reactive with the virus according to the invention or antigenic material of the virus and therefore suitable for the detection of HBS-associated porcine parvovirus infection may also e.g. comprise a standard ELISA test. In such a test the walls of the wells of an ELISA plate can e.g. be coated with the virus according to the invention or antigenic material thereof. After incubation with the material to be tested, e.g. serum of an animal suspected from being infected with the novel porcine parvovirus according to the invention, labeled antibodies reactive with the virus according to the invention are added to the wells. If anti-HBS-associated porcine parvovirus antibodies would be present in the tested serum, these antibodies will bind to the viruses coated to the wells of the ELISA. As a consequence the later added labeled antibodies reactive with the virus would not bind and no color reaction would be found. A lack of color reaction would thus reveal the presence of antibodies reactive with the virus according to the invention.

Therefore, still another embodiment of the present invention relates to diagnostic test kits for the detection of antibodies reactive with the virus according to the invention or with antigenic material of the virus that comprise the virus according to the invention or antigenic material thereof.

The design of the immunoassay may vary. For example, the immunoassay may be based upon competition or direct reaction. Furthermore, protocols may use solid supports or may use cellular material. The detection of the antibody-antigen complex may involve the use of labeled antibodies; the labels may be, for example, enzymes, fluorescent-, chemoluminescent-, radio-active- or dye molecules.

Suitable methods for the detection of antibodies reactive with a virus according to the present invention in the sample include, in addition to the ELISA mentioned above, immunofluorescence test (IFT) and Western blot analysis.

An alternative but quick and easy diagnostic test for diagnosing the presence or absence of a virus according to the invention is a PCR test as referred to above, comprising a PCR primer set reactive with a specific region of the CP or the NS1 gene of HBS-associated porcine parvovirus. Specific in this context means unique for e.g. the CP or the NS1 gene of HBS-associated porcine parvovirus, i.e. not present in other members of the family Parvoviridae.

Preferably such a test would use the primer set (SEQ ID NO: 5-6) that specifically reacts with the Capsid Protein of the virus or the primer set (SEQ ID NO: 7-8) specifically reactive with the NS1 of the virus.

It goes without saying, that more primers can be used than the primers identified above. The present invention provides for the first time the unique sequence of the CP and the NS1 gene of HBS-associated porcine parvovirus. This allows the skilled person to select without any additional efforts, other selective primers. By simple computer-analysis of the CP or the NS1 gene of HBS-associated porcine parvovirus gene sequence provided by the present invention with the, known, CP or NS1 gene of other, non-HBS-associated, porcine parvovirus members of the family Parvoviridae, the skilled person is able to develop other specific PCR-primers for diagnostic tests for the detection of a HBS-associated porcine parvovirus and/or the discrimination between an HBS-associated porcine parvovirus and other viral (porcine) pathogens.

PCR-primers that specifically react with the CP or the NS1 gene of HBS-associated porcine parvovirus are understood to be those primers that react only with the CP or the NS1 gene of HBS-associated porcine parvovirus and not with the CP or the NS1 gene of another (porcine) pathogenic virus, or group of (porcine) pathogenic viruses.

Thus, another embodiment relates to a diagnostic test kit for the detection of a virus according to the invention, characterised in that said test kit comprises a PCR primer set that is specifically reactive with a region of the CP or the NS1 gene of HBS-associated porcine parvovirus.

A preferred form of this embodiment relates to a diagnostic test kit for the detection of a virus according to the invention, characterised in that said test comprises the primer set as depicted in SEQ ID NO: 5-6 or the primer set as depicted in SEQ ID NO: 7-8.

EXAMPLES

Example 1: Analysis of Diseased Animals of Samples Set 1

Description of Sample Set 1

Sample set 1: 17 animals, 16 male/1 female pigs, aged 18-27 weeks. 7 Farms. Received 31 Jul. 2013. Clinical symptoms: Animals suddenly developed abdominal distension, some of them screamed before dying. There were no symptoms noted during the weeks before death. The timing between the observation of first symptoms and death was 2-6 hours. After onset of symptoms, animals were euthanized by electrocution and necropsied.

Organ symptoms: Abnormalities in small intestine. Hemorrhagic symptoms, thin intestinal wall, bloody fluid in intestines. No abnormalities in other organs, except for enlarged, red-appearing, oedemic lymph nodes. See FIG. 3.

Organs were frozen at −70° C. Serum was prepared from clotted blood by centrifugation at 3000×g and subsequent storage at −70° C.

PCR Protocols:

Isolated DNA was screened by PCR using primers derived from the viral sequences (table 1). PCRs were performed using standard methods with an annealing temperature of 58° C. for the Bowl_ORF1_774_F/1626R primer set, and 52° C. for the Bowl_Q_ORF2_FW/REV primer set. A probe was designed for Q-PCR (table 1). Q-PCR was done using standard method with an annealing temperature of 50° C. Q-PCR data was analysed using Bio-Rad CFX Manager 2.0.

TABLE 1

| Primer sequences Bowl | | |
|---|---|---|
| Primer/probe: | Sequence (5'-3'): | SEQ ID NO: |
| Bowl_ORF1_774_F | TGTTGAGTGTGGTGGATTGG | SEQ ID NO: 7 |
| Bowl_ORF1_1626_R | AAGGAAGCTGGACCGAGAG | SEQ ID NO: 8 |
| Bowl_Q_ORF2_FW | CTACATCTGCGCCTGAC | SEQ ID NO: 5 |
| Bowl_Q_ORF2_REV | GTGGTGAGAAGGCAAGAC | SEQ ID NO: 6 |
| Bowl_Q_ORF2_PROBE | 6FAM-CACGAGCTAGAGCGTGCTAAACAG-BHQ1 | SEQ ID NO: 9 |

Results PCR Analysis:

The results of the PCR analysis are depicted in Table 2. In total, 76% of the samples was found positive.

TABLE 2

Results analysis of samples of set 1.

| | Animal number | | | | | | | | | |
|---|---|---|---|---|---|---|---|---|---|---|
| | 1 | 2 | 3 | 4 | 5 | 6 | 7 | 8 | 9 | 10 |
| Sex | M | M | M | M | M | M | M | M | M | F |
| Age (weeks) | 19 | 23 | 23 | 18 | 20 | 19 | 18 | 23 | 26 | 18 |
| Location | 13-3A | 13-3A | 13-3A | 10-3A | 10-3A | 3-3 | 3-3 | 13-3A | 5-3 | 10-3A |
| serum | − | − | + | − | n/a | − | − | + | − | − |
| rectal swap | − | + | − | − | − | − | − | − | − | − |
| blood | − | + | + | − | − | − | − | − | − | + |
| lymph node | − | + | + | + | − | n/a | n/a | + | + | − |
| overall | − | + | + | + | − | − | − | + | + | + |

| | Animal number | | | | | | | total | per- |
|---|---|---|---|---|---|---|---|---|---|
| | 11 | 12 | 13 | 14 | 15 | 16 | 17 | score | centage |
| Sex | M | M | M | M | M | M | M | | |
| Age (weeks) | 23 | 20 | 23 | 18 | 25 | 22 | 27 | | |
| Location | 13-3A | 10-3A | 12-3B | 12-3B | 12-3B | 8-3 | 11-3B | | |
| serum | n/a | n/a | − | + | − | + | + | 5/14 | 36 |
| rectal swap | − | − | − | − | − | − | − | 1/17 | 6 |
| blood | + | − | + | + | − | + | + | 8/17 | 47 |
| lymph node | + | + | + | + | + | + | + | 12/15 | 80 |
| overall | + | + | + | + | + | + | + | 13/17 | 76 |

+: positive for new *parvovirus*.

− negative for new *parvovirus*

Example 2: Analysis of Diseased Animals of Samples Set 2

Description of Sample Set 2

16 animals, 13 male/3 female pigs, aged 12-26 weeks. 7 Farms, 4 additional farms compared to sample set 1 (total of 11 farm in sample set 1+2). Received 22 Aug. 2013.

Clinical symptoms: Animals suddenly developed abdominal distension, some of them screamed before dying. There were no symptoms noted during the weeks before death. The timing between the observation of first symptoms and death was 2-6 hours. After onset of symptoms, animals were euthanized by electrocution prior and necropsied.

Organ symptoms: Abnormalities in small intestine. Hemorrhagic symptoms, thin intestinal wall, bloody fluid in intestines. No abnormalities in other organs, except for enlarged, red-appearing, oedemic lymph nodes. See FIG. 3. Not all lymph nodes and blood samples were tested.

Organs were frozen at −70° C. Serum was prepared from clotted blood by centrifugation at 3000×g and subsequent storage at −70° C.

PCR Protocols:

Isolated DNA was screened by PCR using primers derived from the viral sequences (table 1). PCRs were performed using standard methods with an annealing temperature of 58° C. for the Bowl_ORF1_774_F/1626R primer set, and 52° C. for the Bowl_Q_ORF2_FW/REV primer set. A probe was designed for Q-PCR (table 1). Q-PCR was done using standard method with an annealing temperature of 50° C. Q-PCR data was analysed using Bio-Rad CFX Manager 2.0.

Results PCR Analysis:

The results of the PCR analysis are depicted in Table 3. In total, 25% of the samples was found positive. Blood was not analysed. Only two lymph nodes were analysed.

Example 3: Replication of New Parvovirus in Pigs

Preparation of Animal Material:

Frozen organ material and feces of sample sets 1 and 2 were stored at −70° C. prior to analysis. All procedures were carried out on ice. Organs were defrosted and subsequently homogenized (10% w/v) in tissue culture medium. The homogenate was freeze-thawed once (−70° C.). Subsequently, the homogenate was centrifuged and filtered on 5 μm, 0.45 μm and 0.22 μm filters to remove remaining tissue material.

The filtered homogenate was stored at −70° C. until inoculation.

Inoculums (A or B) were given as a 4×2 mL IM dose (4 different organs, left neck, right neck, left leg, right leg) and an oral dose of 20 mL (10 feces homogenate +4×2.5 ml homogenate of different organs). Inoculums were administered at room temperature.

Inoculum A: Animal 10 Sample Set 2 (See Example 2)

Feces, Lymph nodes, Lung, Spleen, Intestine

Inoculum B: Animal 2 Sample Set 1 (See Example 1)

Feces, Lymph nodes, Lung, Kidney, Liver

Animals

Thirteen pigs (5 Boars/8 gilts/Landrace/high health status/SPF/12-14 weeks of age at time of inoculation) were bred and raised at the MSD farm in Stevensbeek, the Netherlands and housed according to institutional guidelines. The animals were screened for presence of the new parvovirus in serum, feces, nasal swabs and eye swabs prior to inoculation as described in Example 1. One male animal was sacrificed as control animal (not infected). The other twelve pigs were housed in 3 separate groups.

TABLE 3

Results analysis of samples of set 2.

| | Animal number | | | | | | | | | |
|---|---|---|---|---|---|---|---|---|---|---|
| | 1 | 2 | 3 | 4 | 5 | 6 | 7 | 8 | 9 | 10 |
| Sex | M | F | F | F | M | M | M | M | M | M |
| Age (weeks) | 19 | 12 | 23 | 22 | 26 | 26 | 24 | 18 | 18 | 22 |
| Location | 17-3E | 9-3B | 9-3B | 9-3B | 12-3B | 12-3B | 12-3B | 13-3B | 13-3B | 13-3A |
| serum | − | − | − | − | − | − | − | + | + | + |
| rectal swap | − | − | − | − | − | − | − | − | − | + |
| blood | n/a | n/a | n/a | n/a | n/a | n/a | n/a | n/a | n/a | n/a |
| lymph node | n/a | n/a | n/a | n/a | n/a | n/a | n/a | − | n/a | + |
| overall | − | − | − | − | − | − | − | + | + | + |

| | Animal number | | | | | | total | per- |
|---|---|---|---|---|---|---|---|---|
| | 11 | 12 | 13 | 14 | 15 | 16 | score | centage |
| Sex | M | M | M | M | M | M | | |
| Age (weeks) | 22 | 20 | 20 | 24 | 21 | 22 | | |
| Location | 13-3A | 3-3 | 3-3 | 1-3B | 1-3B | 1-3B | | |
| serum | + | − | − | − | − | − | 4/16 | 25 |
| rectal swap | − | − | − | − | − | − | 1/16 | 6 |
| blood | n/a | n/a | n/a | n/a | n/a | n/a | 0/0 | 0 |
| lymph node | n/a | n/a | n/a | n/a | n/a | n/a | 1/2 | 50 |
| overall | + | − | − | − | − | − | 4/16 | 25 |

+: positive for new *parvovirus*.

− negative for new *parvovirus*

Treatment

Group 1: Five Animals

Three animals received inoculum A, two served as contact sentinels

Group 2: Four Animals

Three animals received inoculum B, two served as contact sentinel

Group 3: Three Animals

Three animals received inoculum B

Sampling and Necropsy

Group 1, 2:

Blood samples, rectal/nasal/eye swabs on day −3, 0, 7, 14, 21, 28 after inoculation (if not sacrificed)

Rectal/nasal/eye swabs on day 3, 10, 17, 24 after inoculation (if not sacrificed)

Group 3:

Blood samples, rectal/nasal/eye swabs on day −4, 0, 3, 6 after inoculation (if not sacrificed)

Based on the PCR results, the animals were scheduled for necropsy:

Group 1:

Inoculated: day 10 p.i.; day 25 p.i.; day 31 p.i.

Sentinel: day 18 p.i.; day 31 p.i

Group 2:

Inoculated: day 14 p.i.; day 29 p.i (2 animals)

Sentinel: day 22 p.i.

Group 3:

Inoculated: day 4 p.i. (1 animal); day 7 p.i. (2 animals).

Results

PCR

Animal 10 sample set 2 used for inoculum:

All organs tested positive for new parvovirus: Feces, Lymph nodes, Lung, Spleen, Intestine, Kidney, Liver Animal 2 sample set 1 used for inoculum:

All organs tested positive for new parvovirus: Feces, Lymph nodes, Lung, Kidney, Liver Animal Experiment Result of PCR on swabs/sera: Table 4A-B-C Organ samples were taken for histology, for PCR analysis and for virus isolation. Organs for virus isolation were stored at −70° C. Hepatic lymph nodes (10% homogenates) were analysed using PCR.

Group 1: all inoculated animals serum + (positive) on day 7

Sentinel serum − (negative) on day 7

Swabs: see Table 4A

Group 2: all inoculated animals serum + on day 7

Sentinel serum − on day 7

Swabs: see Table 4B

Group 3: all inoculated animals serum + on day 4

Swabs: see Table 4C

PCR Results

| Necropsied organ | d. 10 p.i. (inoculum A, group 1) | d. 14 p.i. (inoculum B, group 2) |
|---|---|---|
| Serum | positive | positive |
| Spleen | positive | positive |
| Mesenteric Lymph Node | positive | positive |
| Hepatic Lymph Node | positive | positive |
| Inguinal Lymph Node | positive | positive |
| Lung | positive | positive |
| Tonsil | positive | positive |
| Kidney | positive | positive |
| Nasal mucosa | positive | positive |
| Large Intestine | positive | positive |
| Liver | positive | positive |
| Small Intestine | positive | positive |

-continued

| Necropsied organ | d. 10 p.i. (inoculum A, group 1) | d. 14 p.i. (inoculum B, group 2) |
|---|---|---|
| Stomach | positive | positive |
| Brain | positive | positive |
| Bile | weakly positive | weakly positive |
| 50% Small Intestine Content | not detected | not detected |
| 25% Large Intestine Content | not detected | not detected |
| Urine | not detected | not detected |

Results Lymph Nodes

Hepatic lymph nodes of all 13 animals collected at time of necropsy were homogenized 10% (w/v) in culture medium. DNA was isolated from the homogenate and presence of virus was analysed by PCR. The control lymph node was negative for new parvovirus, all 12 inoculated or sentinel pigs were positive for virus.

Conclusion:

On the basis of the data presented above, it can be concluded that the new parvovirus replicates in pigs.

The route of transmission most likely oral/nasal via direct contact, but oral/fecal transmission and transmission through the air cannot be excluded. Fecal excretion is however limited.

The virus is found in multiple organs.

Based on the combined results in Example 1-3 it is expected that in a subset of animals; in about 1-2% of total infected animals, infection with the new parvovirus causes disease around the time of appearance of the virus in the blood (viremia). Shedding in the feces is minimal, but virus remains present in the blood >30 days after infection. Also nasal and eye swabs remain PCR positive >30 days after infection. In the infected pigs as described in Example 3, no hemorrhagic bowel syndrome was observed, but this was to be expected, based on both a low incidence of the disease; 1-2% in general population and the fact that the animals used in Example 3 were relatively young and in excellent condition. They had, other than pigs in a commercial farm setting, no predisposing risk factors.

TABLE 4A

Results group 1: 3 infected animals and 2 sentinels, Inoculum A

| | | day post inoculation | | | | | | | | | |
|---|---|---|---|---|---|---|---|---|---|---|---|
| Animal | Sample | −3 | 0 | 3 | 7 | 10 | 14 | 17 | 21 | 24 | 28 |
| BOWL 1 | R | − | − | − | + | + | − | − | − | − | − |
| BOWL 1 | N | − | − | − | + | + | − | + | + | + | − |
| BOWL 1 | E | − | − | − | + | − | + | + | + | − | − |
| BOWL 1 | S | n/a | − | n/a | + | n/a | + | n/a | + | n/a | + |
| BOWL 2 | R | − | − | − | + | − | | | | | |
| BOWL 2 | N | − | − | − | + | + | | | | | |
| BOWL 2 | E | − | − | − | + | − | | | | | |
| BOWL 2 | S | n/a | − | n/a | + | + | | | | | |
| BOWL 3 | R | − | − | − | + | − | − | − | − | − | |
| BOWL 3 | N | − | − | − | + | + | − | + | + | + | |
| BOWL 3 | E | − | − | − | + | − | + | + | − | + | |
| BOWL 3 | S | n/a | − | n/a | + | n/a | + | n/a | + | n/a | |
| sentinel 1 | R | − | − | − | − | − | − | − | | | |
| sentinel 1 | N | − | − | − | + | − | − | + | | | |
| sentinel 1 | E | − | − | − | + | − | − | + | | | |
| sentinel 1 | S | n/a | − | n/a | − | n/a | + | n/a | | | |

TABLE 4A-continued

Results group 1: 3 infected animals and 2 sentinels, Inoculum A

| | | day post inoculation | | | | | | | | | |
|---|---|---|---|---|---|---|---|---|---|---|---|
| Animal | Sample | −3 | 0 | 3 | 7 | 10 | 14 | 17 | 21 | 24 | 28 |
| sentinel 2 | R | − | − | − | − | − | − | − | + | − | − |
| sentinel 2 | N | − | − | − | + | − | − | + | + | + | + |
| sentinel 2 | E | − | − | − | + | − | + | + | − | − | + |
| sentinel 2 | S | n/a | − | n/a | − | n/a | + | n/a | + | n/a | + |

The novel *porcine parvovirus* according to the invention is referred to as "BOWL".
R: rectal swab
N: nasal swab
E: eye swab
S: serum
n/a: not analysed (not sampled)

TABLE 4B

Results group 2: 3 infected animals and 1 sentinel, Inoculum B

| | | day post inoculation | | | | | | | | | |
|---|---|---|---|---|---|---|---|---|---|---|---|
| Animal | Sample | −3 | 0 | 3 | 7 | 10 | 14 | 17 | 21 | 24 | 28 |
| BOWL 1 | R | − | − | − | − | + | − | | | | |
| BOWL 1 | N | − | − | − | + | + | + | | | | |
| BOWL 1 | E | − | − | − | + | + | + | | | | |
| BOWL 1 | S | n/a | − | n/a | + | n/a | + | | | | |
| BOWL 2 | R | − | − | − | + | − | − | − | − | − | − |
| BOWL 2 | N | − | − | − | + | − | − | + | + | + | − |
| BOWL 2 | E | − | − | − | + | + | + | + | − | − | + |
| BOWL 2 | S | n/a | − | n/a | + | n/a | + | n/a | + | n/a | + |
| BOWL 3 | R | − | − | − | − | − | − | − | − | − | − |
| BOWL 3 | N | − | − | − | + | + | + | + | + | + | + |
| BOWL 3 | E | − | − | − | + | + | + | + | − | − | − |
| BOWL 3 | S | n/a | − | n/a | + | n/a | + | n/a | + | n/a | + |
| sentinel 1 | R | − | − | − | − | + | − | − | − | | |
| sentinel 1 | N | − | − | − | + | + | − | + | + | | |
| sentinel 1 | E | − | − | − | + | − | + | + | − | | |
| sentinel 1 | S | n/a | − | n/a | − | n/a | + | n/a | + | | |

The novel *porcine parvovirus* according to the invention is referred to as "BOWL".
R: rectal swab
N: nasal swab
E: eye swab
S: serum
n/a: not analysed (not sampled)

TABLE 4C

Results group 3: 3 infected animals, Inoculum B

| | | day post inoculation | | | |
|---|---|---|---|---|---|
| Animal | Sample | −4 | 0 | 3 | 6 |
| BOWL 1 | R | − | − | − | − |
| BOWL 1 | N | − | − | − | + |
| BOWL 1 | E | − | − | − | + |
| BOWL 1 | S | − | − | + | + |
| BOWL 2 | R | − | − | − | |
| BOWL 2 | N | − | − | − | |
| BOWL 2 | E | − | − | − | |
| BOWL 2 | S | − | − | + | |
| BOWL 3 | R | − | − | − | − |
| BOWL 3 | N | − | − | − | + |
| BOWL 3 | E | − | − | − | − |
| BOWL 3 | S | − | − | + | + |

The novel *porcine parvovirus* according to the invention is referred to as "BOWL".
R: rectal swab
N: nasal swab
E: eye swab
S: serum
n/a: not analysed (not sampled)

LEGEND TO THE FIGURES

FIG. 1: phylogenetic tree indicating the relatedness of the NS1 of the novel porcine parvovirus according to the invention, to the NS1 of other parvoviruses. The novel porcine parvovirus according to the invention is referred to as "BOWL".

FIG. 2: phylogenetic tree indicating the relatedness of the Capsid Protein of the novel porcine parvovirus according to the invention, to the Capsid Protein of other parvoviruses. The novel porcine parvovirus according to the invention is referred to as "BOWL".

Figure 3:
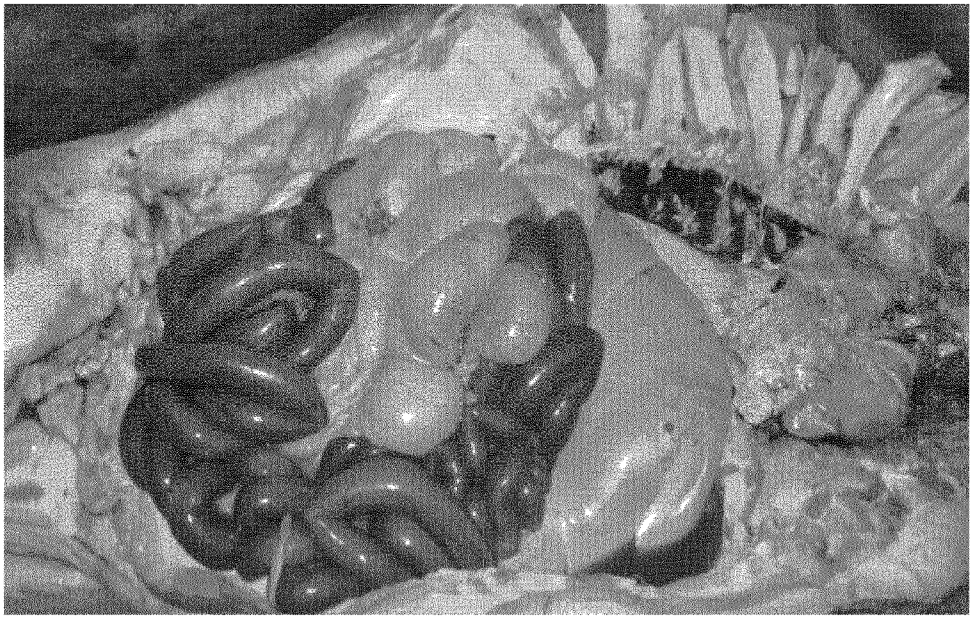

FIG. 3: example of hemorrhagic bowel syndrome as seen in Sample set 1 and 2

LITERATURE REFERENCES

1) Harris, Hank. "Hemorrhagic Bowel Syndrome in Pigs—Digestive System." Merck Veterinary Manual, 2018, merckvetmanual.com/digestive-system/intestinal-diseases-in-pigs/hemorrhagic-bowel-syndrome-in-pigs.
2) Häni et al. (1993) Schweiz Arch Tierheilkd. 135:117-124
3) "People. Pigs. Planet." Pork Checkoff, pork.org.
4) Streck et al., Journal of General Virology 92: 2628-2636 (2011)
5) Ren et al., Virus research 178: 392-397 (2013)
6) Xiao et al., Veterinary Microbiology 161: 325-330 (2013)
7) Opriessnig et al., Veterinary Microbiology 163: 177-183 (2013)
8) Chenbin Li et al., Archives of Virology 158: 1987-1991 (2013)
9) Xiao et al., Veterinary Microbiology 160: 290-296 (2012)
10) Cadar et al., Archives of Virology 156: 2233-2239 (2011)
11) Lau et al., Journal of General Virology 89: 1840-1848 (2008)
12) Cheung et al., Archives of Virology 155: 801-806 (2010)
13) Huang et al., Virology Journal 7: 333-336 (2010)
14) Cheung et al., Archives of Virology 156: 2071-2078 (2011)
15) Xiao et al., PLoS One 8: e65312. (2013)
16) Xiao et al., Genome Announcements 1:e00021-12. (2013)
17) Cheng et al., PLoS One 5: e13583. (2010)
18) Martinez et al., Vaccine 10: 684-690 (1992)
19) Casal et al., Biotechnology and Applied Biochemistry 29: 141-150 (1999)
20) Zhou et al, Virology Journal 7: 366 (2010)
21) Hao Feng, PlosOne; Jan. 17, 2014, DOI: 10.1371/journal.pone.007957
22) Saliki et al., Journ. Gen. Virol. 73: 369-74 (1992)
23) Brown et al., Journ. of Virol. 65: 2702 (1991)
24) Baculovirus Expression Vectors, A Laboratory Manual. By David R. O'Reilly, Lois K. Miller, and Verne A. Luckow. Publisher: Oxford University Press, USA ISBN-10: 0195091310 (Sep. 23, 1993), ISBN-13: 978-0195091311 (May 1994).
25) Baculovirus and Insect Cell Expression Protocols. In: Methods in Molecular Biology™, Volume 388 (2007). Editors: David W. Murhammer. ISBN: 978-1-58829-537-8 (Print) 978-1-59745-457-5 (Online)
26) Fujisaki, Y., and Murikami, Y (1982). "Immunity to infection with porcine parvovirus in pigs inoculated with attenuated HT-strain". *Natl Inst Anim Health* (Tokyo) 22: 36-37
27) Chen et al., Virology Journal 8:307 (2011)
28) Mayer et al., Vaccine 22: 317-328 (2004)

29) Production of recombinant proteins: novel microbial and eukaryotic expression systems by Gerd Gellissen, ISBN: 3-527-31036-3

30) Gerdts et al, Journal of General Virology 78: 2139-2146 (1997)

31) Gorres et al., Clinical Vaccine Immunology 18: 1987-1995 (2011)

32) Paul & Mengeling, Am. J. Vet. Res.: 41: 2007-2011 (1980)

33) Paul & Mengeling, Am. J. Vet. Res.: 45: 2481-2485 (1984)

34) Fujisaki e& Murakami, Nat. Inst. of Animal Health quarterly (Tokyo) 22: 36-37 (1982)

35) Mayer and Walter, eds Immunochemical Methods in Cell and Molecular Biology, Academic Press, London, 1987)

36) Kohler and Milstein, Nature, 256: 495-497 (1975)

37) Qiu et al., J. Virol. 79: 11035-11044 (2005)

38) Wang et al., J. Virol. Meth. 200: 41-46 (2014)

39) Guan et al., J. Virol. 83: 9541-9553 (2009)

The invention claimed is:

1. A DNA fragment comprising a gene encoding a Capsid Protein (CP) wherein the nucleotide sequence of said gene has at least 80% identity to the nucleotide sequence of SEQ ID NO: 1.

2. The CP encoded by the DNA fragment of claim 1.

3. A DNA fragment comprising a gene encoding a non-structural protein 1 (NS1), wherein the nucleotide sequence of said gene has at least 80% identity to the nucleotide sequence of SEQ ID NO: 3.

4. The NS1 encoded by the DNA fragment of claim 3.

5. The DNA fragment of claim 1, wherein the CP gene is under the control of a functional heterologous promoter.

6. An immortalized cell culture comprising an isolated virus which is a member of the sub-family Parvovirinae of the family of the Parvoviridae, said virus being characterized in that:

a) the virus has a viral genome comprising a gene encoding a Capsid Protein (CP) and a gene encoding a non-structural protein 1 (NS1), wherein
  a) the CP is encoded by a nucleic acid sequence of SEQ ID NO: 1, or
  b) the CP is encoded by a nucleic acid sequence 90% identical to SEQ ID NO: 1, which encodes a polypeptide of SEQ ID NO: 2;
  and wherein:
  a) the NS1 is encoded by a nucleic acid sequence of SEQ ID NO: 3, or
  b) the NS1 is encoded by a nucleic acid sequence 90% identical to SEQ ID NO: 3, which encodes a polypeptide of SEQ ID NO: 4; and a pharmaceutically acceptable carrier selected from the group consisting of saline or aqueous buffers.

7. A method of generating an immune response in a mammal, comprising administering an immunologically-effective amount of isolated virus which is a member of the sub-family Parvovirinae of the family of the Parvoviridae, said virus being characterized in that:

a) the virus has a viral genome comprising a gene encoding a Capsid Protein (CP) and a gene encoding a non-structural protein 1 (NS1), wherein
  a) the CP is encoded by a nucleic acid sequence of SEQ ID NO: 1, or
  b) the CP is encoded by a nucleic acid sequence 90% identical to SEQ ID NO: 1, which encodes a polypeptide of SEQ ID NO: 2;
  and wherein:
  a) the NS1 encoded by a nucleic acid sequence of SEQ ID NO: 3, or
  b) the NS1 is encoded by a nucleic acid sequence 90% identical to SEQ ID NO: 3, which encodes a polypeptide of SEQ ID NO: 4; and a pharmaceutically acceptable carrier selected from the group consisting of saline or aqueous buffers.

8. An immortalized cell culture comprising an isolated virus which is a member of the sub-family Parvovirinae of the family of the Parvoviridae, said virus being characterized in that:

a) the virus has a viral genome comprising a gene encoding a Capsid Protein (CP) and a gene encoding a non-structural protein 1 (NS1), wherein
  a) the CP is encoded by a nucleic acid sequence of SEQ ID NO: 1, or
  b) the CP is encoded by a nucleic acid sequence 90% identical to SEQ ID NO: 1;
  and wherein:
  a) the NS1 is encoded by a nucleic acid sequence of SEQ ID NO: 3, or
  b) the NS1 is encoded by a nucleic acid sequence 90% identical to SEQ ID NO: 3; and a pharmaceutically acceptable carrier selected from e group consisting of saline or aqueous buffers.

9. A method of generating an immune response in a mammal, comprising administering an immunologically-effective amount of isolated virus which is a member of the sub-family Parvovirinae of the family of the Parvoviridae, said virus being characterized in that:

a) the virus has a viral genome comprising a gene encoding a Capsid Protein (CP) and a gene encoding a non-structural protein 1 (NS1), wherein
   a) the CP is encoded by a nucleic acid sequence of SEQ ID NO: 1, or
   b) the CP is encoded by a nucleic acid sequence 90% identical to SEQ ID NO: 1;
   and wherein:
   a) the NS1 is encoded by a nucleic acid sequence of SEQ ID NO: 3, or
   b) the NS1 is encoded by a nucleic acid sequence 90% identical to SEQ ID NO: 3; and a pharmaceutically acceptable carrier selected from the group consisting of saline or aqueous buffers.

10. A method of generating an immune response in a mammal, comprising administering an immunologically-effective amount of an empty capsid protein of a virus which is a member of the sub-family Parvovirinae of the family of the Parvoviridae, said virus being characterized in that:

a) the virus has a viral genome comprising a gene encoding a Capsid Protein (CP) and a gene encoding a non-structural protein 1 (NS1), wherein
   a) the CP is encoded by a nucleic acid sequence of SEQ ID NO: 1, or
   b) the CP is encoded by a nucleic acid sequence 90% identical to SEQ ID NO: 1;
   and wherein:
   a) the NS1 is encoded by a nucleic acid sequence of SEQ ID NO: 3, or
   b) the NS1 is encoded by a nucleic acid sequence 90% identical to SEQ ID NO: 3; and a pharmaceutically acceptable carrier selected from the group consisting of saline or aqueous buffers.

11. A method of generating an immune response in a mammal according to claim 10, characterized in that the empty capsid protein is baculovirus expressed.

* * * * *

SEQUENCE LISTING

```
<160> NUMBER OF SEQ ID NOS: 10

<210> SEQ ID NO 1
<211> LENGTH: 3570
<212> TYPE: DNA
<213> ORGANISM: Porcine parvovirus
<220> FEATURE:
<221> NAME/KEY: CDS
<222> LOCATION: (1)..(3570)

<400> SEQUENCE: 1

atg agc cgt tct act caa aga gat ctt tgg tct ttg tta agg gag aga       48
Met Ser Arg Ser Thr Gln Arg Asp Leu Trp Ser Leu Leu Arg Glu Arg
1               5                   10                  15

ctt gaa agg tat aag gat cga gtt aaa tat tat ggt att ttg gtg cca       96
Leu Glu Arg Tyr Lys Asp Arg Val Lys Tyr Tyr Gly Ile Leu Val Pro
            20                  25                  30

gaa cgt cct tct acc tta gca tct tat ttt agt aaa gac cca cct cca      144
Glu Arg Pro Ser Thr Leu Ala Ser Tyr Phe Ser Lys Asp Pro Pro Pro
        35                  40                  45

gat cct cca act gtt aaa ttt gat aaa ccc tat cag gat gta gat aga      192
Asp Pro Pro Thr Val Lys Phe Asp Lys Pro Tyr Gln Asp Val Asp Arg
    50                  55                  60

ttc tgg ttt cca aca gac gat tat agt gac tgg tat gtc tgg cat gga      240
Phe Trp Phe Pro Thr Asp Asp Tyr Ser Asp Trp Tyr Val Trp His Gly
65                  70                  75                  80

gag gac aga cct cct aga ttt acc gag cat tcc ggt gtt cag ggt ttt      288
Glu Asp Arg Pro Pro Arg Phe Thr Glu His Ser Gly Val Gln Gly Phe
                85                  90                  95

aaa act agg tgt gag ggg ggg ctt cct tta atg ccc agt gat ccc aaa      336
Lys Thr Arg Cys Glu Gly Gly Leu Pro Leu Met Pro Ser Asp Pro Lys
            100                 105                 110

ttt tgc ccc ata caa aat ttt tgg gat cag ttc gct aat ttt gat gag      384
Phe Cys Pro Ile Gln Asn Phe Trp Asp Gln Phe Ala Asn Phe Asp Glu
        115                 120                 125

ggg tct ccg tcc acc cag atc ggt gag agt gtt tca tgg agt gat cat      432
Gly Ser Pro Ser Thr Gln Ile Gly Glu Ser Val Ser Trp Ser Asp His
    130                 135                 140

ttt gga agt ccc gat ccc tct cat cat cag gag gtg agg gat gct gat      480
Phe Gly Ser Pro Asp Pro Ser His His Gln Glu Val Arg Asp Ala Asp
145                 150                 155                 160

gaa gtt act tcc gag cgg cag caa tat aaa aat agg att gtc acc tta      528
Glu Val Thr Ser Glu Arg Gln Gln Tyr Lys Asn Arg Ile Val Thr Leu
                165                 170                 175

tta aga aaa gtt tat tgg gct aag cag tgg tct ggg aaa tta caa att      576
Leu Arg Lys Val Tyr Trp Ala Lys Gln Trp Ser Gly Lys Leu Gln Ile
            180                 185                 190

aat gtt cct tcc ctc gaa agc ctt tat gag cag atc ccc tat atg cta      624
Asn Val Pro Ser Leu Glu Ser Leu Tyr Glu Gln Ile Pro Tyr Met Leu
        195                 200                 205
```

-continued

```
gcc tat atg gac gct gat aat tgg cgt cag aat ttg tta gct gct aaa      672
Ala Tyr Met Asp Ala Asp Asn Trp Arg Gln Asn Leu Leu Ala Ala Lys
    210                 215                 220

act ctg cga acc act ttg gaa gca ttt tcc tgt gtt cca gat cct tcc      720
Thr Leu Arg Thr Thr Leu Glu Ala Phe Ser Cys Val Pro Asp Pro Ser
225                 230                 235                 240

acg tgc gat gtc aca atc tcc aca ccc cta tct ggt gaa acg gat ccc      768
Thr Cys Asp Val Thr Ile Ser Thr Pro Leu Ser Gly Glu Thr Asp Pro
                245                 250                 255

gcc tct ttt gca aaa tac tta tgt tcc ctt gta tgc aac agg tct caa      816
Ala Ser Phe Ala Lys Tyr Leu Cys Ser Leu Val Cys Asn Arg Ser Gln
            260                 265                 270

gaa aaa gaa cag gcg cag acg cct tct ttg tct cca tct aaa caa gaa      864
Glu Lys Glu Gln Ala Gln Thr Pro Ser Leu Ser Pro Ser Lys Gln Glu
        275                 280                 285

ggg cag atg tca agt cct gat tct gca tcg atc tcc caa cct ccc cct      912
Gly Gln Met Ser Ser Pro Asp Ser Ala Ser Ile Ser Gln Pro Pro Pro
    290                 295                 300

gaa agt cac aag gat aga ctg ctt cct aaa act gat ccc ctt cag gaa      960
Glu Ser His Lys Asp Arg Leu Leu Pro Lys Thr Asp Pro Leu Gln Glu
305                 310                 315                 320

gca ggg ccc att ccc gct ccc ccc aca gct cag aag cct att atc tct     1008
Ala Gly Pro Ile Pro Ala Pro Pro Thr Ala Gln Lys Pro Ile Ile Ser
                325                 330                 335

aag ggt gca ggc ggt gga ggg tct tct ggc ttc ata atc cct cca aaa     1056
Lys Gly Ala Gly Gly Gly Gly Ser Ser Gly Phe Ile Ile Pro Pro Lys
            340                 345                 350

cct cct agc ccc gat cac cct aaa gat ccc ccc cct cct cct cct ccc     1104
Pro Pro Ser Pro Asp His Pro Lys Asp Pro Pro Pro Pro Pro Pro Pro
        355                 360                 365

tct cca att cct cct tct aca tct gcg cct gac gca gaa aag cac gag     1152
Ser Pro Ile Pro Pro Ser Thr Ser Ala Pro Asp Ala Glu Lys His Glu
    370                 375                 380

cta gag cgt gct aaa cag gag aaa caa gag gaa gat gag ctc atg cac     1200
Leu Glu Arg Ala Lys Gln Glu Lys Gln Glu Glu Asp Glu Leu Met His
385                 390                 395                 400

aga atc aaa tca gga gaa gga gaa gga gaa cga gga ggc ctc gtc ttg     1248
Arg Ile Lys Ser Gly Glu Gly Glu Gly Glu Arg Gly Gly Leu Val Leu
                405                 410                 415

cct tct cac cac tac act ggt cct aga aat cct gtc cca gct ggc aag     1296
Pro Ser His His Tyr Thr Gly Pro Arg Asn Pro Val Pro Ala Gly Lys
            420                 425                 430

cct gct gac ccc gtt gat gaa tct tct gcg aga cat gac atc agg tat     1344
Pro Ala Asp Pro Val Asp Glu Ser Ser Ala Arg His Asp Ile Arg Tyr
        435                 440                 445

ggg caa cgt ctt aaa cat gga gac tgg cca tac ctg tgg ggg aag gac     1392
Gly Gln Arg Leu Lys His Gly Asp Trp Pro Tyr Leu Trp Gly Lys Asp
    450                 455                 460

ttg gat aat gct cag cga gat gag att atc aaa gct ctt cat agt cat     1440
Leu Asp Asn Ala Gln Arg Asp Glu Ile Ile Lys Ala Leu His Ser His
465                 470                 475                 480

gtc aaa gtg gga acc caa ttg gca ggg aat ata gtg agg agt att tgg     1488
Val Lys Val Gly Thr Gln Leu Ala Gly Asn Ile Val Arg Ser Ile Trp
                485                 490                 495

aag gct aag gag ctc tta aca gaa cct gtg tat gag ctg tta aag tct     1536
Lys Ala Lys Glu Leu Leu Thr Glu Pro Val Tyr Glu Leu Leu Lys Ser
            500                 505                 510

att ctc cct cct tca gat tta tct aaa gtt cct ctt cct cat tcc caa     1584
Ile Leu Pro Pro Ser Asp Leu Ser Lys Val Pro Leu Pro His Ser Gln
        515                 520                 525
```

-continued

```
cag aca gac aga aca gaa gat cca gaa act cca ggg gag act aga gga      1632
Gln Thr Asp Arg Thr Glu Asp Pro Glu Thr Pro Gly Glu Thr Arg Gly
    530                 535                 540

act gga tca gac agt cct cga tct cct cgg cct tct gga tca act gaa      1680
Thr Gly Ser Asp Ser Pro Arg Ser Pro Arg Pro Ser Gly Ser Thr Glu
545                 550                 555                 560

gac ggg gga ggt cct tct tcc gag tcc aga tta cct ggg act aaa gtt      1728
Asp Gly Gly Gly Pro Ser Ser Glu Ser Arg Leu Pro Gly Thr Lys Val
                565                 570                 575

cca gta gac cca tct gcc acc acg tcc gaa gca aag agg cag agg act      1776
Pro Val Asp Pro Ser Ala Thr Thr Ser Glu Ala Lys Arg Gln Arg Thr
            580                 585                 590

gag gag ggg atg gac ata tct tct tgc tgt cca ggg ggg att tct gct      1824
Glu Glu Gly Met Asp Ile Ser Ser Cys Cys Pro Gly Gly Ile Ser Ala
        595                 600                 605

tct ggg gct gct tca aat aac tct ggt ctt gct tgt ggg ggt ggg ggg      1872
Ser Gly Ala Ala Ser Asn Asn Ser Gly Leu Ala Cys Gly Gly Gly Gly
    610                 615                 620

ggt act aat tta ggg aca gaa tct ctt gta tcc ggc tgt cag ttt ggt      1920
Gly Thr Asn Leu Gly Thr Glu Ser Leu Val Ser Gly Cys Gln Phe Gly
625                 630                 635                 640

aaa aac tct gtg atc act tca tct ttt aga cga tgt ctc att tca ccc      1968
Lys Asn Ser Val Ile Thr Ser Ser Phe Arg Arg Cys Leu Ile Ser Pro
                645                 650                 655

tgg cct gat aaa tac tgt tgt tct tct gct cac gat ctt att ccc gga      2016
Trp Pro Asp Lys Tyr Cys Cys Ser Ser Ala His Asp Leu Ile Pro Gly
            660                 665                 670

gtg gtc tac gag acc cct tgg tgc tat tat gat ctg aac gtc atc tca      2064
Val Val Tyr Glu Thr Pro Trp Cys Tyr Tyr Asp Leu Asn Val Ile Ser
        675                 680                 685

gca cat ttt tct cct tct gct tgg cag agg ctt ttg gag gat tat gat      2112
Ala His Phe Ser Pro Ser Ala Trp Gln Arg Leu Leu Glu Asp Tyr Asp
    690                 695                 700

gcc ttt cga cct aaa tcc ctt aaa gtt acc atc cag tct tta gtt ttt      2160
Ala Phe Arg Pro Lys Ser Leu Lys Val Thr Ile Gln Ser Leu Val Phe
705                 710                 715                 720

aaa gat gtc tgt caa ggt gca gaa aaa caa act aca gtt cag gat tcc      2208
Lys Asp Val Cys Gln Gly Ala Glu Lys Gln Thr Thr Val Gln Asp Ser
                725                 730                 735

cag tca gcc acc att gct atc ttt gag gat aaa gac tat gac tac ccc      2256
Gln Ser Ala Thr Ile Ala Ile Phe Glu Asp Lys Asp Tyr Asp Tyr Pro
            740                 745                 750

tat gtg atg gga ggg ggt caa aaa aca gtt ccg ggt cac ttg ccc ggt      2304
Tyr Val Met Gly Gly Gly Gln Lys Thr Val Pro Gly His Leu Pro Gly
        755                 760                 765

caa cct tat aat ctt ccc aag tat tct tac aga acc ctt ggt tca gtc      2352
Gln Pro Tyr Asn Leu Pro Lys Tyr Ser Tyr Arg Thr Leu Gly Ser Val
    770                 775                 780

aaa gaa agt aat agg gcc agt atg ggc ggt tca ggg tac act ttc aaa      2400
Lys Glu Ser Asn Arg Ala Ser Met Gly Gly Ser Gly Tyr Thr Phe Lys
785                 790                 795                 800

tcc aat caa gat acg gaa ttg ttt ctg ctt gaa aca cat gat gcc act      2448
Ser Asn Gln Asp Thr Glu Leu Phe Leu Leu Glu Thr His Asp Ala Thr
                805                 810                 815

ctt att cga ggc ggg ggt act ttt gag cag tac tat gaa ttt cca aac      2496
Leu Ile Arg Gly Gly Gly Thr Phe Glu Gln Tyr Tyr Glu Phe Pro Asn
            820                 825                 830

gat ctt cct ttc gaa aat ttg act cag tat cct tgg gat atc cgc cgt      2544
Asp Leu Pro Phe Glu Asn Leu Thr Gln Tyr Pro Trp Asp Ile Arg Arg
```

-continued

```
        835                 840                 845

cag gat aac ccc ctc tat cag cag agg atc act gtc atg tca ggt tct      2592
Gln Asp Asn Pro Leu Tyr Gln Gln Arg Ile Thr Val Met Ser Gly Ser
    850                 855                 860

gac aga gat acg gta ggc att tta gat gga gat ttt tac tct cct ttt      2640
Asp Arg Asp Thr Val Gly Ile Leu Asp Gly Asp Phe Tyr Ser Pro Phe
865                 870                 875                 880

cgg ttc aaa ggt cat gat aga ccc gcc atg tgg ctg cca gga cag agg      2688
Arg Phe Lys Gly His Asp Arg Pro Ala Met Trp Leu Pro Gly Gln Arg
                885                 890                 895

ttg att cag ggc aaa ttc ata gat acg cac cca ata ccc aat aca ggg      2736
Leu Ile Gln Gly Lys Phe Ile Asp Thr His Pro Ile Pro Asn Thr Gly
            900                 905                 910

agg agt ggg gtt cat cct aat gat ttt cac aca agg ggc gat ggt cat      2784
Arg Ser Gly Val His Pro Asn Asp Phe His Thr Arg Gly Asp Gly His
        915                 920                 925

ggt gac acc cat aga aca cat gaa gag agg atc tac agt cta gat aca      2832
Gly Asp Thr His Arg Thr His Glu Glu Arg Ile Tyr Ser Leu Asp Thr
    930                 935                 940

ggt ctt gct gct atg cca cgt gcc gct cat aga ccc acc ctt cag ccc      2880
Gly Leu Ala Ala Met Pro Arg Ala Ala His Arg Pro Thr Leu Gln Pro
945                 950                 955                 960

gga cct agg act ctg tct cat gcc gta cgc aga ccc gat ggt tcc acc      2928
Gly Pro Arg Thr Leu Ser His Ala Val Arg Arg Pro Asp Gly Ser Thr
                965                 970                 975

gtg gtc acg gct aat gcg tgt gct tac gct tac acc cag gag aat cct      2976
Val Val Thr Ala Asn Ala Cys Ala Tyr Ala Tyr Thr Gln Glu Asn Pro
            980                 985                 990

cat cag gaa ccc tgg agt gat ctc  aat gtc aga cat acc  atg tat agg    3024
His Gln Glu Pro Trp Ser Asp Leu  Asn Val Arg His Thr  Met Tyr Arg
        995                 1000                 1005

tta gcc  tat caa cgt caa aaa  ggt ttt cag caa ccc  ggg gac cct      3069
Leu Ala  Tyr Gln Arg Gln Lys  Gly Phe Gln Gln Pro  Gly Asp Pro
    1010                 1015                 1020

ctt cat  att cga acc cat gct  tgt tat ggg gac ggg  gat gtt acc      3114
Leu His  Ile Arg Thr His Ala  Cys Tyr Gly Asp Gly  Asp Val Thr
    1025                 1030                 1035

att cca  aaa gaa gag tcc tta  tgg cct act gtt ctg  ggt agt tgc      3159
Ile Pro  Lys Glu Glu Ser Leu  Trp Pro Thr Val Leu  Gly Ser Cys
    1040                 1045                 1050

aca gaa  aag tcc cct gcc tgt  tta gag tcc cag att  tgg tgt aaa      3204
Thr Glu  Lys Ser Pro Ala Cys  Leu Glu Ser Gln Ile  Trp Cys Lys
    1055                 1060                 1065

aca cca  aat gtg gac atg gtc  tat gga gaa cac aca  ccc cct ctt      3249
Thr Pro  Asn Val Asp Met Val  Tyr Gly Glu His Thr  Pro Pro Leu
    1070                 1075                 1080

gct tta  tgg ggt atg cat gct  ccc cca ccc cat gta  ttt ctc agg      3294
Ala Leu  Trp Gly Met His Ala  Pro Pro Pro His Val  Phe Leu Arg
    1085                 1090                 1095

atg ctt  gct caa gag ggt cct  cct aat gtc agt act  tgc aga ccg      3339
Met Leu  Ala Gln Glu Gly Pro  Pro Asn Val Ser Thr  Cys Arg Pro
    1100                 1105                 1110

gct caa  tct ggt cag acc ttc  atc aat caa tat ggt  cag ttt ctc      3384
Ala Gln  Ser Gly Gln Thr Phe  Ile Asn Gln Tyr Gly  Gln Phe Leu
    1115                 1120                 1125

ctc tgt  ttt acc atg gta tgg  gaa gtt aag cct aga  ccc aag tcc      3429
Leu Cys  Phe Thr Met Val Trp  Glu Val Lys Pro Arg  Pro Lys Ser
    1130                 1135                 1140

atc aag  caa tgg aat cca cgt  ccg ccc atc agc att  cct gtt ggt      3474
```

-continued

```
Ile Lys Gln Trp Asn Pro Arg Pro Pro Ile Ser Ile Pro Val Gly
    1145                1150                1155

cag tct ggt cct gct ttc att ctc gat caa gat ggc tac tac cgt      3519
Gln Ser Gly Pro Ala Phe Ile Leu Asp Gln Asp Gly Tyr Tyr Arg
    1160                1165                1170

ctc cca gaa cat gtc tgg tct gcc agg gaa cgt atc cgc agc aaa      3564
Leu Pro Glu His Val Trp Ser Ala Arg Glu Arg Ile Arg Ser Lys
    1175                1180                1185

cgc tag                                                          3570
Arg


<210> SEQ ID NO 2
<211> LENGTH: 1189
<212> TYPE: PRT
<213> ORGANISM: Porcine parvovirus

<400> SEQUENCE: 2

Met Ser Arg Ser Thr Gln Arg Asp Leu Trp Ser Leu Leu Arg Glu Arg
1               5                   10                  15

Leu Glu Arg Tyr Lys Asp Arg Val Lys Tyr Tyr Gly Ile Leu Val Pro
            20                  25                  30

Glu Arg Pro Ser Thr Leu Ala Ser Tyr Phe Ser Lys Asp Pro Pro Pro
        35                  40                  45

Asp Pro Pro Thr Val Lys Phe Asp Lys Pro Tyr Gln Asp Val Asp Arg
    50                  55                  60

Phe Trp Phe Pro Thr Asp Asp Tyr Ser Asp Trp Tyr Val Trp His Gly
65                  70                  75                  80

Glu Asp Arg Pro Pro Arg Phe Thr Glu His Ser Gly Val Gln Gly Phe
                85                  90                  95

Lys Thr Arg Cys Glu Gly Gly Leu Pro Leu Met Pro Ser Asp Pro Lys
            100                 105                 110

Phe Cys Pro Ile Gln Asn Phe Trp Asp Gln Phe Ala Asn Phe Asp Glu
        115                 120                 125

Gly Ser Pro Ser Thr Gln Ile Gly Glu Ser Val Ser Trp Ser Asp His
    130                 135                 140

Phe Gly Ser Pro Asp Pro Ser His His Gln Glu Val Arg Asp Ala Asp
145                 150                 155                 160

Glu Val Thr Ser Glu Arg Gln Gln Tyr Lys Asn Arg Ile Val Thr Leu
                165                 170                 175

Leu Arg Lys Val Tyr Trp Ala Lys Gln Trp Ser Gly Lys Leu Gln Ile
            180                 185                 190

Asn Val Pro Ser Leu Glu Ser Leu Tyr Glu Gln Ile Pro Tyr Met Leu
        195                 200                 205

Ala Tyr Met Asp Ala Asp Asn Trp Arg Gln Asn Leu Leu Ala Ala Lys
    210                 215                 220

Thr Leu Arg Thr Thr Leu Glu Ala Phe Ser Cys Val Pro Asp Pro Ser
225                 230                 235                 240

Thr Cys Asp Val Thr Ile Ser Thr Pro Leu Ser Gly Glu Thr Asp Pro
                245                 250                 255

Ala Ser Phe Ala Lys Tyr Leu Cys Ser Leu Val Cys Asn Arg Ser Gln
            260                 265                 270

Glu Lys Glu Gln Ala Gln Thr Pro Ser Leu Ser Pro Ser Lys Gln Glu
        275                 280                 285

Gly Gln Met Ser Ser Pro Asp Ser Ala Ser Ile Ser Gln Pro Pro Pro
    290                 295                 300
```

-continued

```
Glu Ser His Lys Asp Arg Leu Leu Pro Lys Thr Asp Pro Leu Gln Glu
305                 310                 315                 320

Ala Gly Pro Ile Pro Ala Pro Pro Thr Ala Gln Lys Pro Ile Ile Ser
                325                 330                 335

Lys Gly Ala Gly Gly Gly Gly Ser Ser Gly Phe Ile Ile Pro Pro Lys
            340                 345                 350

Pro Pro Ser Pro Asp His Pro Lys Asp Pro Pro Pro Pro Pro Pro Pro
        355                 360                 365

Ser Pro Ile Pro Pro Ser Thr Ser Ala Pro Asp Ala Glu Lys His Glu
    370                 375                 380

Leu Glu Arg Ala Lys Gln Glu Lys Gln Glu Glu Asp Glu Leu Met His
385                 390                 395                 400

Arg Ile Lys Ser Gly Glu Gly Glu Gly Glu Arg Gly Gly Leu Val Leu
                405                 410                 415

Pro Ser His His Tyr Thr Gly Pro Arg Asn Pro Val Pro Ala Gly Lys
            420                 425                 430

Pro Ala Asp Pro Val Asp Glu Ser Ser Ala Arg His Asp Ile Arg Tyr
        435                 440                 445

Gly Gln Arg Leu Lys His Gly Asp Trp Pro Tyr Leu Trp Gly Lys Asp
    450                 455                 460

Leu Asp Asn Ala Gln Arg Asp Glu Ile Ile Lys Ala Leu His Ser His
465                 470                 475                 480

Val Lys Val Gly Thr Gln Leu Ala Gly Asn Ile Val Arg Ser Ile Trp
                485                 490                 495

Lys Ala Lys Glu Leu Leu Thr Glu Pro Val Tyr Glu Leu Leu Lys Ser
            500                 505                 510

Ile Leu Pro Pro Ser Asp Leu Ser Lys Val Pro Leu Pro His Ser Gln
        515                 520                 525

Gln Thr Asp Arg Thr Glu Asp Pro Glu Thr Pro Gly Glu Thr Arg Gly
    530                 535                 540

Thr Gly Ser Asp Ser Pro Arg Ser Pro Arg Pro Ser Gly Ser Thr Glu
545                 550                 555                 560

Asp Gly Gly Gly Pro Ser Ser Glu Ser Arg Leu Pro Gly Thr Lys Val
                565                 570                 575

Pro Val Asp Pro Ser Ala Thr Thr Ser Glu Ala Lys Arg Gln Arg Thr
            580                 585                 590

Glu Glu Gly Met Asp Ile Ser Ser Cys Cys Pro Gly Gly Ile Ser Ala
        595                 600                 605

Ser Gly Ala Ala Ser Asn Asn Ser Gly Leu Ala Cys Gly Gly Gly Gly
    610                 615                 620

Gly Thr Asn Leu Gly Thr Glu Ser Leu Val Ser Gly Cys Gln Phe Gly
625                 630                 635                 640

Lys Asn Ser Val Ile Thr Ser Ser Phe Arg Arg Cys Leu Ile Ser Pro
                645                 650                 655

Trp Pro Asp Lys Tyr Cys Cys Ser Ser Ala His Asp Leu Ile Pro Gly
            660                 665                 670

Val Val Tyr Glu Thr Pro Trp Cys Tyr Tyr Asp Leu Asn Val Ile Ser
        675                 680                 685

Ala His Phe Ser Pro Ser Ala Trp Gln Arg Leu Leu Glu Asp Tyr Asp
    690                 695                 700

Ala Phe Arg Pro Lys Ser Leu Lys Val Thr Ile Gln Ser Leu Val Phe
705                 710                 715                 720

Lys Asp Val Cys Gln Gly Ala Glu Lys Gln Thr Thr Val Gln Asp Ser
```

-continued

```
                725                 730                 735

Gln Ser Ala Thr Ile Ala Ile Phe Glu Asp Lys Asp Tyr Asp Tyr Pro
            740                 745                 750

Tyr Val Met Gly Gly Gly Gln Lys Thr Val Pro Gly His Leu Pro Gly
        755                 760                 765

Gln Pro Tyr Asn Leu Pro Lys Tyr Ser Tyr Arg Thr Leu Gly Ser Val
    770                 775                 780

Lys Glu Ser Asn Arg Ala Ser Met Gly Gly Ser Gly Tyr Thr Phe Lys
785                 790                 795                 800

Ser Asn Gln Asp Thr Glu Leu Phe Leu Leu Glu Thr His Asp Ala Thr
                805                 810                 815

Leu Ile Arg Gly Gly Gly Thr Phe Glu Gln Tyr Tyr Glu Phe Pro Asn
            820                 825                 830

Asp Leu Pro Phe Glu Asn Leu Thr Gln Tyr Pro Trp Asp Ile Arg Arg
        835                 840                 845

Gln Asp Asn Pro Leu Tyr Gln Gln Arg Ile Thr Val Met Ser Gly Ser
    850                 855                 860

Asp Arg Asp Thr Val Gly Ile Leu Asp Gly Asp Phe Tyr Ser Pro Phe
865                 870                 875                 880

Arg Phe Lys Gly His Asp Arg Pro Ala Met Trp Leu Pro Gly Gln Arg
                885                 890                 895

Leu Ile Gln Gly Lys Phe Ile Asp Thr His Pro Ile Pro Asn Thr Gly
            900                 905                 910

Arg Ser Gly Val His Pro Asn Asp Phe His Thr Arg Gly Asp Gly His
        915                 920                 925

Gly Asp Thr His Arg Thr His Glu Glu Arg Ile Tyr Ser Leu Asp Thr
    930                 935                 940

Gly Leu Ala Ala Met Pro Arg Ala Ala His Arg Pro Thr Leu Gln Pro
945                 950                 955                 960

Gly Pro Arg Thr Leu Ser His Ala Val Arg Arg Pro Asp Gly Ser Thr
                965                 970                 975

Val Val Thr Ala Asn Ala Cys Ala Tyr Ala Tyr Thr Gln Glu Asn Pro
            980                 985                 990

His Gln Glu Pro Trp Ser Asp Leu  Asn Val Arg His Thr  Met Tyr Arg
        995                 1000                1005

Leu Ala  Tyr Gln Arg Gln Lys  Gly Phe Gln Gln Pro  Gly Asp Pro
    1010                1015                1020

Leu His  Ile Arg Thr His Ala  Cys Tyr Gly Asp Gly  Asp Val Thr
    1025                1030                1035

Ile Pro  Lys Glu Glu Ser Leu  Trp Pro Thr Val Leu  Gly Ser Cys
    1040                1045                1050

Thr Glu  Lys Ser Pro Ala Cys  Leu Glu Ser Gln Ile  Trp Cys Lys
    1055                1060                1065

Thr Pro  Asn Val Asp Met Val  Tyr Gly Glu His Thr  Pro Pro Leu
    1070                1075                1080

Ala Leu  Trp Gly Met His Ala  Pro Pro Pro His Val  Phe Leu Arg
    1085                1090                1095

Met Leu  Ala Gln Glu Gly Pro  Pro Asn Val Ser Thr  Cys Arg Pro
    1100                1105                1110

Ala Gln  Ser Gly Gln Thr Phe  Ile Asn Gln Tyr Gly  Gln Phe Leu
    1115                1120                1125

Leu Cys  Phe Thr Met Val Trp  Glu Val Lys Pro Arg  Pro Lys Ser
    1130                1135                1140
```

-continued

```
Ile Lys  Gln Trp Asn Pro Arg  Pro Pro Ile Ser Ile  Pro Val Gly
    1145                 1150                 1155

Gln Ser  Gly Pro Ala Phe Ile  Leu Asp Gln Asp Gly  Tyr Tyr Arg
    1160                 1165                 1170

Leu Pro  Glu His Val Trp Ser  Ala Arg Glu Arg Ile  Arg Ser Lys
    1175                 1180                 1185

Arg


<210> SEQ ID NO 3
<211> LENGTH: 1989
<212> TYPE: DNA
<213> ORGANISM: Porcine parvovirus
<220> FEATURE:
<221> NAME/KEY: CDS
<222> LOCATION: (1)..(1989)

<400> SEQUENCE: 3

atg tct cag acc ttc tgg acg ggt att tgc agg ctt ttc cct gat att       48
Met Ser Gln Thr Phe Trp Thr Gly Ile Cys Arg Leu Phe Pro Asp Ile
1               5                   10                  15

ggg aag att cct ggg gtg act cct gag cgg tat att tat gct gta aac       96
Gly Lys Ile Pro Gly Val Thr Pro Glu Arg Tyr Ile Tyr Ala Val Asn
            20                  25                  30

gtg agt acc cgt aat ggg caa aag tgg ccg aaa gtt ggg acc gag ggg      144
Val Ser Thr Arg Asn Gly Gln Lys Trp Pro Lys Val Gly Thr Glu Gly
        35                  40                  45

cca ttg gct gca ggt gtc tta cag ggg gag gcc ctt ttc cgt gag acc      192
Pro Leu Ala Ala Gly Val Leu Gln Gly Glu Ala Leu Phe Arg Glu Thr
    50                  55                  60

ctt aaa gag gtc cgg aag gtg tgc cgg ctg ccg caa gac ccc cat ctt      240
Leu Lys Glu Val Arg Lys Val Cys Arg Leu Pro Gln Asp Pro His Leu
65                  70                  75                  80

ttc ttt caa ttg gag aaa gtt gat tcc aaa ggg ggt ctt cac ctt cat      288
Phe Phe Gln Leu Glu Lys Val Asp Ser Lys Gly Gly Leu His Leu His
                85                  90                  95

ttt tgt att agt gtt gct gct ggc act cct aga gat gtg tct tcg atg      336
Phe Cys Ile Ser Val Ala Ala Gly Thr Pro Arg Asp Val Ser Ser Met
            100                 105                 110

ttt aaa gcc att gag cgt cga gtt tcc ttt tac tac ttt ggt gta gag      384
Phe Lys Ala Ile Glu Arg Arg Val Ser Phe Tyr Tyr Phe Gly Val Glu
        115                 120                 125

ggc ttg act ttt ttt act cct cat aaa aat aag cat ggt gct tgg aag      432
Gly Leu Thr Phe Phe Thr Pro His Lys Asn Lys His Gly Ala Trp Lys
    130                 135                 140

agt aat gat gag ggc ttt att gtg aat tat ctt ctt aaa aaa ttg cct      480
Ser Asn Asp Glu Gly Phe Ile Val Asn Tyr Leu Leu Lys Lys Leu Pro
145                 150                 155                 160

ttg tct gag tgt gtg tat gcg tgg act aat atg gat ggg gtg att ggc      528
Leu Ser Glu Cys Val Tyr Ala Trp Thr Asn Met Asp Gly Val Ile Gly
                165                 170                 175

gat gcc tgt ctg aat gaa gat aag cgc agg gaa ttg ttg tct gag cgt      576
Asp Ala Cys Leu Asn Glu Asp Lys Arg Arg Glu Leu Leu Ser Glu Arg
            180                 185                 190

caa gat cag gga gtc att aaa gag ctc act gct cct act ttt aaa gct      624
Gln Asp Gln Gly Val Ile Lys Glu Leu Thr Ala Pro Thr Phe Lys Ala
        195                 200                 205

gct acg ggt gat aaa atg ttg agt gtg gtg gat tgg atg tgt gat aat      672
Ala Thr Gly Asp Lys Met Leu Ser Val Val Asp Trp Met Cys Asp Asn
    210                 215                 220
```

-continued

```
gat gtg act acg gag cgc cga tgg gag gaa ata tcg gct gcg tcc ctg      720
Asp Val Thr Thr Glu Arg Arg Trp Glu Glu Ile Ser Ala Ala Ser Leu
225                 230                 235                 240

tac tct ttc ctt gct acc cca gct ggc act cat ttg gct aaa cag tgt      768
Tyr Ser Phe Leu Ala Thr Pro Ala Gly Thr His Leu Ala Lys Gln Cys
                245                 250                 255

ctt aga gct gcg aat cag cgt att gtg agc act aaa cct ctt ggt ttg      816
Leu Arg Ala Ala Asn Gln Arg Ile Val Ser Thr Lys Pro Leu Gly Leu
            260                 265                 270

agt ctc tgt aaa ttt gcc agt gaa aag gag ctt cgt gct ttt caa aat      864
Ser Leu Cys Lys Phe Ala Ser Glu Lys Glu Leu Arg Ala Phe Gln Asn
        275                 280                 285

ggg gat cct gag ttg tct tca gac aac aat agg atc tat tac tta ttt      912
Gly Asp Pro Glu Leu Ser Ser Asp Asn Asn Arg Ile Tyr Tyr Leu Phe
    290                 295                 300

gct atg aat aat tac tgc cct gat atg gcc agt atg att ttc ttt tgg      960
Ala Met Asn Asn Tyr Cys Pro Asp Met Ala Ser Met Ile Phe Phe Trp
305                 310                 315                 320

tgg tct atg cgc caa acg ggt aag aga aac agt att tgg ctg ttt gga     1008
Trp Ser Met Arg Gln Thr Gly Lys Arg Asn Ser Ile Trp Leu Phe Gly
                325                 330                 335

cct gct aca acc ggt aaa acc aat tta gca agt gct att gca cat act     1056
Pro Ala Thr Thr Gly Lys Thr Asn Leu Ala Ser Ala Ile Ala His Thr
            340                 345                 350

gct gcc agt tat ggg tgt gtt aac tgg aat aac gca aat ttc ccg ttt     1104
Ala Ala Ser Tyr Gly Cys Val Asn Trp Asn Asn Ala Asn Phe Pro Phe
        355                 360                 365

caa gac att gtg aat gtg caa ctg ggt tgg tgg gag gaa gga aag atg     1152
Gln Asp Ile Val Asn Val Gln Leu Gly Trp Trp Glu Glu Gly Lys Met
    370                 375                 380

aca gag gat gtg gtt gaa tgt gct aag gca ttg cta ggg gga agt aat     1200
Thr Glu Asp Val Val Glu Cys Ala Lys Ala Leu Leu Gly Gly Ser Asn
385                 390                 395                 400

gta aga gtt gac cgc aaa tgt atg caa tct gcg gaa gtg caa tct cct     1248
Val Arg Val Asp Arg Lys Cys Met Gln Ser Ala Glu Val Gln Ser Pro
                405                 410                 415

cct ttt att att aca tcc aat acg gat atg tgc ctt gtt tct caa ggc     1296
Pro Phe Ile Ile Thr Ser Asn Thr Asp Met Cys Leu Val Ser Gln Gly
            420                 425                 430

agt tac atc agt ttt gag cac cag cag cct ctc cag gat aga atg att     1344
Ser Tyr Ile Ser Phe Glu His Gln Gln Pro Leu Gln Asp Arg Met Ile
        435                 440                 445

aaa ttt gag ttt aac cat gtt ctt cct ggc aat ttc ggc ctc att tct     1392
Lys Phe Glu Phe Asn His Val Leu Pro Gly Asn Phe Gly Leu Ile Ser
    450                 455                 460

gaa gat gaa gtc gtg gcc ttc ttc aga aat ggt gct tat aat gtg ttg     1440
Glu Asp Glu Val Val Ala Phe Phe Arg Asn Gly Ala Tyr Asn Val Leu
465                 470                 475                 480

aag cat gcg tac atg aga aag gcc cag ctt ttt gct ctc ggt cca gct     1488
Lys His Ala Tyr Met Arg Lys Ala Gln Leu Phe Ala Leu Gly Pro Ala
                485                 490                 495

tcc ttg cca tat aag ccc cct acg ggt gaa tta gtg tgt ata gac caa     1536
Ser Leu Pro Tyr Lys Pro Pro Thr Gly Glu Leu Val Cys Ile Asp Gln
            500                 505                 510

gct aag tct cct tct ccc tct gct tct cgc cgc agt gtg aga aat tgg     1584
Ala Lys Ser Pro Ser Pro Ser Ala Ser Arg Arg Ser Val Arg Asn Trp
        515                 520                 525

atg acg tgt ccc cct gat cct gtc cag gac gat ccc gct gaa ctg gac     1632
Met Thr Cys Pro Pro Asp Pro Val Gln Asp Asp Pro Ala Glu Leu Asp
    530                 535                 540
```

```
gag tat ttt cct cca gat act cct cca gtg gat tgt cct tgt cct att     1680
Glu Tyr Phe Pro Pro Asp Thr Pro Pro Val Asp Cys Pro Cys Pro Ile
545                 550                 555                 560

tct cct gtg agg gag tct tgt ccc tcg cca ggg cct tgc cct acc cct     1728
Ser Pro Val Arg Glu Ser Cys Pro Ser Pro Gly Pro Cys Pro Thr Pro
                565                 570                 575

cct cgc aaa aaa caa cgg aag agc aag cat tgc tcc ttg tct gtc tct     1776
Pro Arg Lys Lys Gln Arg Lys Ser Lys His Cys Ser Leu Ser Val Ser
            580                 585                 590

gcg ggt aaa gtt cct gtg gtg gtt gtg ggt gat tct gac tca gtc ccc     1824
Ala Gly Lys Val Pro Val Val Val Val Gly Asp Ser Asp Ser Val Pro
        595                 600                 605

ccc gaa gaa aaa gaa aaa gag gaa gtt tcc gtg ggg gaa tcc cag gat     1872
Pro Glu Glu Lys Glu Lys Glu Glu Val Ser Val Gly Glu Ser Gln Asp
    610                 615                 620

cca caa ctg tac tgg gac cta act ctc agt caa tcc gac gtt cct gtg     1920
Pro Gln Leu Tyr Trp Asp Leu Thr Leu Ser Gln Ser Asp Val Pro Val
625                 630                 635                 640

cct gaa gac gag agt acc cag ttt cct gac gac gct gtg gac gct tct     1968
Pro Glu Asp Glu Ser Thr Gln Phe Pro Asp Asp Ala Val Asp Ala Ser
                645                 650                 655

gat ctc att gct gaa cag tag                                         1989
Asp Leu Ile Ala Glu Gln
            660


<210> SEQ ID NO 4
<211> LENGTH: 662
<212> TYPE: PRT
<213> ORGANISM: Porcine parvovirus

<400> SEQUENCE: 4

Met Ser Gln Thr Phe Trp Thr Gly Ile Cys Arg Leu Phe Pro Asp Ile
1               5                   10                  15

Gly Lys Ile Pro Gly Val Thr Pro Glu Arg Tyr Ile Tyr Ala Val Asn
            20                  25                  30

Val Ser Thr Arg Asn Gly Gln Lys Trp Pro Lys Val Gly Thr Glu Gly
        35                  40                  45

Pro Leu Ala Ala Gly Val Leu Gln Gly Glu Ala Leu Phe Arg Glu Thr
    50                  55                  60

Leu Lys Glu Val Arg Lys Val Cys Arg Leu Pro Gln Asp Pro His Leu
65                  70                  75                  80

Phe Phe Gln Leu Glu Lys Val Asp Ser Lys Gly Gly Leu His Leu His
                85                  90                  95

Phe Cys Ile Ser Val Ala Ala Gly Thr Pro Arg Asp Val Ser Ser Met
            100                 105                 110

Phe Lys Ala Ile Glu Arg Arg Val Ser Phe Tyr Tyr Phe Gly Val Glu
        115                 120                 125

Gly Leu Thr Phe Phe Thr Pro His Lys Asn Lys His Gly Ala Trp Lys
    130                 135                 140

Ser Asn Asp Glu Gly Phe Ile Val Asn Tyr Leu Leu Lys Lys Leu Pro
145                 150                 155                 160

Leu Ser Glu Cys Val Tyr Ala Trp Thr Asn Met Asp Gly Val Ile Gly
                165                 170                 175

Asp Ala Cys Leu Asn Glu Asp Lys Arg Arg Glu Leu Leu Ser Glu Arg
            180                 185                 190

Gln Asp Gln Gly Val Ile Lys Glu Leu Thr Ala Pro Thr Phe Lys Ala
        195                 200                 205
```

-continued

```
Ala Thr Gly Asp Lys Met Leu Ser Val Val Asp Trp Met Cys Asp Asn
    210                 215                 220

Asp Val Thr Thr Glu Arg Arg Trp Glu Glu Ile Ser Ala Ala Ser Leu
225                 230                 235                 240

Tyr Ser Phe Leu Ala Thr Pro Ala Gly Thr His Leu Ala Lys Gln Cys
                245                 250                 255

Leu Arg Ala Ala Asn Gln Arg Ile Val Ser Thr Lys Pro Leu Gly Leu
            260                 265                 270

Ser Leu Cys Lys Phe Ala Ser Glu Lys Glu Leu Arg Ala Phe Gln Asn
        275                 280                 285

Gly Asp Pro Glu Leu Ser Ser Asp Asn Asn Arg Ile Tyr Tyr Leu Phe
    290                 295                 300

Ala Met Asn Asn Tyr Cys Pro Asp Met Ala Ser Met Ile Phe Phe Trp
305                 310                 315                 320

Trp Ser Met Arg Gln Thr Gly Lys Arg Asn Ser Ile Trp Leu Phe Gly
                325                 330                 335

Pro Ala Thr Thr Gly Lys Thr Asn Leu Ala Ser Ala Ile Ala His Thr
            340                 345                 350

Ala Ala Ser Tyr Gly Cys Val Asn Trp Asn Asn Ala Asn Phe Pro Phe
        355                 360                 365

Gln Asp Ile Val Asn Val Gln Leu Gly Trp Trp Glu Glu Gly Lys Met
    370                 375                 380

Thr Glu Asp Val Val Glu Cys Ala Lys Ala Leu Leu Gly Gly Ser Asn
385                 390                 395                 400

Val Arg Val Asp Arg Lys Cys Met Gln Ser Ala Glu Val Gln Ser Pro
                405                 410                 415

Pro Phe Ile Ile Thr Ser Asn Thr Asp Met Cys Leu Val Ser Gln Gly
            420                 425                 430

Ser Tyr Ile Ser Phe Glu His Gln Gln Pro Leu Gln Asp Arg Met Ile
        435                 440                 445

Lys Phe Glu Phe Asn His Val Leu Pro Gly Asn Phe Gly Leu Ile Ser
    450                 455                 460

Glu Asp Glu Val Val Ala Phe Phe Arg Asn Gly Ala Tyr Asn Val Leu
465                 470                 475                 480

Lys His Ala Tyr Met Arg Lys Ala Gln Leu Phe Ala Leu Gly Pro Ala
                485                 490                 495

Ser Leu Pro Tyr Lys Pro Pro Thr Gly Glu Leu Val Cys Ile Asp Gln
            500                 505                 510

Ala Lys Ser Pro Ser Pro Ser Ala Ser Arg Arg Ser Val Arg Asn Trp
        515                 520                 525

Met Thr Cys Pro Pro Asp Pro Val Gln Asp Asp Pro Ala Glu Leu Asp
    530                 535                 540

Glu Tyr Phe Pro Pro Asp Thr Pro Pro Val Asp Cys Pro Cys Pro Ile
545                 550                 555                 560

Ser Pro Val Arg Glu Ser Cys Pro Ser Pro Gly Pro Cys Pro Thr Pro
                565                 570                 575

Pro Arg Lys Lys Gln Arg Lys Ser Lys His Cys Ser Leu Ser Val Ser
            580                 585                 590

Ala Gly Lys Val Pro Val Val Val Val Gly Asp Ser Asp Ser Val Pro
        595                 600                 605

Pro Glu Glu Lys Glu Lys Glu Glu Val Ser Val Gly Glu Ser Gln Asp
    610                 615                 620
```

-continued

Pro Gln Leu Tyr Trp Asp Leu Thr Leu Ser Gln Ser Asp Val Pro Val
625 630 635 640

Pro Glu Asp Glu Ser Thr Gln Phe Pro Asp Asp Ala Val Asp Ala Ser
645 650 655

Asp Leu Ile Ala Glu Gln
660

<210> SEQ ID NO 5
<211> LENGTH: 17
<212> TYPE: DNA
<213> ORGANISM: Porcine parvovirus

<400> SEQUENCE: 5
ctacatctgc gcctgac 17

<210> SEQ ID NO 6
<211> LENGTH: 18
<212> TYPE: DNA
<213> ORGANISM: Porcine parvovirus

<400> SEQUENCE: 6
gtggtgagaa ggcaagac 18

<210> SEQ ID NO 7
<211> LENGTH: 20
<212> TYPE: DNA
<213> ORGANISM: Porcine parvovirus

<400> SEQUENCE: 7
tgttgagtgt ggtggattgg 20

<210> SEQ ID NO 8
<211> LENGTH: 19
<212> TYPE: DNA
<213> ORGANISM: Porcine parvovirus

<400> SEQUENCE: 8
aaggaagctg gaccgagag 19

<210> SEQ ID NO 9
<211> LENGTH: 24
<212> TYPE: DNA
<213> ORGANISM: Porcine parvovirus

<400> SEQUENCE: 9
cacgagctag agcgtgctaa acag 24

<210> SEQ ID NO 10
<211> LENGTH: 5999
<212> TYPE: DNA
<213> ORGANISM: Porcine parvovirus

<400> SEQUENCE: 10
ttaatggacc aataggattt acttctgctt tttagggtat aaaagttcgt acttctgctt 60
tttccctcat tctgtgcttg ggagctgatc tgtttagatc tttttgcttc tctgcgccga 120
aagcctctgt attatgtctc agaccttctg gacgggtatt tgcaggcttt tccctgatat 180
tgggaagatt cctggggtga ctcctgagcg gtatatttat gctgtaaacg tgagtacccg 240
taatgggcaa aagtggccga aagttgggac cgaggggcca ttggctgcag gtgtcttaca 300
gggggaggcc cttttccgtg agacccttaa agaggtccgg aaggtgtgcc ggctgccgca 360

-continued

```
agacccccat cttttctttc aattggagaa agttgattcc aaagggggtc ttcaccttca    420
tttttgtatt agtgttgctg ctggcactcc tagagatgtg tcttcgatgt ttaaagccat    480
tgagcgtcga gtttcctttt actactttgg tgtagagggc ttgacttttt ttactcctca    540
taaaaataag catggtgctt ggaagagtaa tgatgagggc tttattgtga attatcttct    600
taaaaaattg cctttgtctg agtgtgtgta tgcgtggact aatatggatg gggtgattgg    660
cgatgcctgt ctgaatgaag ataagcgcag ggaattgttg tctgagcgtc aagatcaggg    720
agtcattaaa gagctcactg ctcctacttt taaagctgct acgggtgata aaatgttgag    780
tgtggtggat tggatgtgtg ataatgatgt gactacggag cgccgatggg aggaaatatc    840
ggctgcgtcc ctgtactctt tccttgctac cccagctggc actcatttgg ctaaacagtg    900
tcttagagct gcgaatcagc gtattgtgag cactaaacct cttggtttga gtctctgtaa    960
atttgccagt gaaaaggagc ttcgtgcttt tcaaaatggg gatcctgagt tgtcttcaga   1020
caacaatagg atctattact tatttgctat gaataattac tgccctgata tggccagtat   1080
gattttcttt tggtggtcta tgcgccaaac gggtaagaga aacagtattt ggctgtttgg   1140
acctgctaca accggtaaaa ccaatttagc aagtgctatt gcacatactg ctgccagtta   1200
tgggtgtgtt aactggaata acgcaaattt cccgtttcaa gacattgtga atgtgcaact   1260
gggttggtgg gaggaaggaa agatgacaga ggatgtggtt gaatgtgcta aggcattgct   1320
agggggaagt aatgtaagag ttgaccgcaa atgtatgcaa tctgcggaag tgcaatctcc   1380
tccttttatt attacatcca atacggatat gtgccttgtt tctcaaggca gttacatcag   1440
ttttgagcac cagcagcctc tccaggatag aatgattaaa tttgagttta accatgttct   1500
tcctggcaat ttcggcctca tttctgaaga tgaagtcgtg gccttcttca gaaatggtgc   1560
ttataatgtg ttgaagcatg cgtacatgag aaaggcccag ctttttgctc tcggtccagc   1620
ttccttgcca tataagcccc ctacgggtga attagtgtgt atagaccaag ctaagtctcc   1680
ttctccctct gcttctcgcc gcagtgtgag aaattggatg acgtgtcccc ctgatcctgt   1740
ccaggacgat cccgctgaac tggacgagta ttttcctcca gatactcctc cagtggattg   1800
tccttgtcct atttctcctg tgagggagtc ttgtccctcg ccagggcctt gccctacccc   1860
tcctcgcaaa aaacaacgga agagcaagca ttgctccttg tctgtctctg cgggtaaagt   1920
tcctgtggtg gttgtgggtg attctgactc agtccccccc gaagaaaaag aaaaagagga   1980
agtttccgtg gggaatccc aggatccaca actgtactgg gacctaactc tcagtcaatc   2040
cgacgttcct gtgcctgaag acgagagtac ccagtttcct gacgacgctg tggacgcttc   2100
tgatctcatt gctgaacagt agttaaggta tgagccgttc tactcaaaga gatctttggt   2160
ctttgttaag ggagagactt gaaaggtata aggatcgagt taaatattat ggtattttgg   2220
tgccagaacg tccttctacc ttagcatctt attttagtaa agacccacct ccagatcctc   2280
caactgttaa atttgataaa ccctatcagg atgtagatag attctggttt ccaacagacg   2340
attatagtga ctggtatgtc tggcatggag aggacagacc tcctagattt accgagcatt   2400
ccggtgttca gggttttaaa actaggtgtg aggggggggct tcctttaatg cccagtgatc   2460
ccaaattttg ccccatacaa aatttttggg atcagttcgc taattttgat gaggggtctc   2520
cgtccaccca gatcggtgag agtgtttcat ggagtgatca ttttggaagt cccgatccct   2580
ctcatcatca ggaggtgagg gatgctgatg aagttacttc cgagcggcag caatataaaa   2640
ataggattgt caccttatta agaaaagttt attgggctaa gcagtggtct gggaaattac   2700
aaattaatgt tccttccctc gaaagccttt atgagcagat cccctatatg ctagcctata   2760
```

-continued

```
tggacgctga taattggcgt cagaatttgt tagctgctaa aactctgcga accactttgg   2820
aagcattttc ctgtgttcca gatccttcca cgtgcgatgt cacaatctcc acacccctat   2880
ctggtgaaac ggatcccgcc tcttttgcaa aatacttatg ttcccttgta tgcaacaggt   2940
ctcaagaaaa agaacaggcg cagacgcctt ctttgtctcc atctaaacaa gaagggcaga   3000
tgtcaagtcc tgattctgca tcgatctccc aacctccccc tgaaagtcac aaggatagac   3060
tgcttcctaa aactgatccc cttcaggaag cagggcccat tcccgctccc cccacagctc   3120
agaagcctat tatctctaag ggtgcaggcg gtggagggtc ttctggcttc ataatccctc   3180
caaaacctcc tagccccgat caccctaaag atcccccccc tcctcctcct ccctctccaa   3240
ttcctccttc tacatctgcg cctgacgcag aaaagcacga gctagagcgt gctaaacagg   3300
agaaacaaga ggaagatgag ctcatgcaca gaatcaaatc aggagaagga gaaggagaac   3360
gaggaggcct cgtcttgcct tctcaccact acactggtcc tagaaatcct gtcccagctg   3420
gcaagcctgc tgaccccgtt gatgaatctt ctgcgagaca tgacatcagg tatgggcaac   3480
gtcttaaaca tggagactgg ccatacctgt gggggaagga cttggataat gctcagcgag   3540
atgagattat caaagctctt catagtcatg tcaaagtggg aacccaattg gcagggaata   3600
tagtgaggag tatttggaag gctaaggagc tcttaacaga acctgtgtat gagctgttaa   3660
agtctattct ccctccttca gatttatcta aagttcctct tcctcattcc caacagacag   3720
acagaacaga agatccagaa actccagggg agactagagg aactggatca gacagtcctc   3780
gatctcctcg gccttctgga tcaactgaag acgggggagg tccttcttcc gagtccagat   3840
tacctgggac taaagttcca gtagacccat ctgccaccac gtccgaagca aagaggcaga   3900
ggactgagga ggggatggac atatcttctt gctgtccagg ggggatttct gcttctgggg   3960
ctgcttcaaa taactctggt cttgcttgtg ggggtggggg gggtactaat ttagggacag   4020
aatctcttgt atccggctgt cagtttggta aaaactctgt gatcacttca tcttttagac   4080
gatgtctcat ttcaccctgg cctgataaat actgttgttc ttctgctcac gatcttattc   4140
ccggagtggt ctacgagacc ccttggtgct attatgatct gaacgtcatc tcagcacatt   4200
tttctccttc tgcttggcag aggcttttgg aggattatga tgcctttcga cctaaatccc   4260
ttaaagttac catccagtct ttagttttta aagatgtctg tcaaggtgca gaaaaacaaa   4320
ctacagttca ggattcccag tcagccacca ttgctatctt tgaggataaa gactatgact   4380
acccctatgt gatgggaggg ggtcaaaaaa cagttccggg tcacttgccc ggtcaacctt   4440
ataatcttcc caagtattct tacagaaccc ttggttcagt caaagaaagt aatagggcca   4500
gtatgggcgg ttcagggtac actttcaaat ccaatcaaga tacggaattg tttctgcttg   4560
aaacacatga tgccactctt attcgaggcg gggtactttt tgagcagtac tatgaatttc   4620
caaacgatct tcctttcgaa aatttgactc agtatccttg ggatatccgc cgtcaggata   4680
acccccctcta tcagcagagg atcactgtca tgtcaggttc tgacagagat acggtaggca   4740
ttttagatgg agatttttac tctccttttc ggttcaaagg tcatgataga cccgccatgt   4800
ggctgccagg acagaggttg attcagggca aattcataga tacgcaccca atacccaata   4860
cagggaggag tggggttcat cctaatgatt ttcacacaag ggcgatggt catggtgaca   4920
cccatagaac acatgaagag aggatctaca gtctagatac aggtcttgct gctatgccac   4980
gtgccgctca tagacccacc cttcagcccg gacctaggac tctgtctcat gccgtacgca   5040
gacccgatgg ttccaccgtg gtcacggcta atgcgtgtgc ttacgcttac acccaggaga   5100
```

-continued

```
atcctcatca ggaaccctgg agtgatctca atgtcagaca taccatgtat aggttagcct   5160

atcaacgtca aaaaggtttt cagcaacccg gggaccctct tcatattcga acccatgctt   5220

gttatgggga cggggatgtt accattccaa aagaagagtc cttatggcct actgttctgg   5280

gtagttgcac agaaaagtcc cctgcctgtt tagagtccca gatttggtgt aaaacaccaa   5340

atgtggacat ggtctatgga gaacacacac cccctcttgc tttatggggt atgcatgctc   5400

ccccacccca tgtatttctc aggatgcttg ctcaagaggg tcctcctaat gtcagtactt   5460

gcagaccggc tcaatctggt cagaccttca tcaatcaata tggtcagttt ctcctctgtt   5520

ttaccatggt atgggaagtt aagcctagac ccaagtccat caagcaatgg aatccacgtc   5580

cgcccatcag cattcctgtt ggtcagtctg gtcctgcttt cattctcgat caagatggct   5640

actaccgtct cccagaacat gtctggtctg ccagggaacg tatccgcagc aaacgctagt   5700

gcccccagca atacacttac tacagtattg atgtgtcagg cattctggtt gattgtttta   5760

ttttggctcc gcctactgta tggcccatgt aaacgcatct attatgaaaa taaaatacgt   5820

caattgctga tgtaattcgt gttgtaattc ttgtttgaaa agcgcatatt ttcttgccgg   5880

tctgagtaac accacctatg acatcatata aatttgatta cgtaacttcc tctttttact   5940

tcctcttttt tgattggatt tacgcaatat cacaattcta gcagttatct gagcgggct    5999
```